United States Patent
Freeman et al.

(10) Patent No.: US 12,213,937 B2
(45) Date of Patent: *Feb. 4, 2025

(54) ACTIVE COMPRESSION DECOMPRESSION CARDIOPULMONARY RESUSCITATION CHEST COMPRESSION FEEDBACK

(71) Applicant: ZOLL Medical Corporation, Chelmsford, MA (US)

(72) Inventors: Gary A. Freeman, Waltham, MA (US); Guy R. Johnson, Gloucester, MA (US); James R. Homuth, Corcoran, MN (US); Keith Lurie, Minneapolis, MN (US); Anja Metzger, Lake Elmo, MN (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/200,702

(22) Filed: May 23, 2023

(65) Prior Publication Data

US 2023/0363976 A1 Nov. 16, 2023

Related U.S. Application Data

(63) Continuation of application No. 17/344,343, filed on Jun. 10, 2021, now Pat. No. 11,701,295, which is a
(Continued)

(51) Int. Cl.
*A61H 31/00* (2006.01)
*A61H 31/02* (2006.01)
*G16H 20/30* (2018.01)
*G16H 20/40* (2018.01)

(52) U.S. Cl.
CPC .......... *A61H 31/005* (2013.01); *A61H 31/02* (2013.01); *G16H 20/30* (2018.01); *G16H 20/40* (2018.01);
(Continued)

(58) Field of Classification Search
CPC .... A61H 31/00; A61H 31/004; A61H 31/005; A61H 31/006; A61H 31/007;
(Continued)

(56) References Cited

U.S. PATENT DOCUMENTS

| 7,220,235 B2 | 5/2007 | Geheb et al. |
| 8,798,743 B1 | 8/2014 | Khuon et al. |

(Continued)

*Primary Examiner* — Justine R Yu
*Assistant Examiner* — Matthew R Moon
(74) *Attorney, Agent, or Firm* — Mintz Levin Cohn Ferris Glovsky and Popeo, P.C.

(57) ABSTRACT

Systems and methods related to the field of cardiac resuscitation, and in particular to devices for assisting rescuers in performing cardio-pulmonary resuscitation (CPR) are described herein. The system includes an applicator device configured to provide ACD CPR treatment to a patient's chest according to a plurality of phases at least one sensor configured to be coupled to the patient's chest and to measure at least one parameter related to the ACD CPR treatment and information for determining whether at least one transition point of the ACD CPR treatment has been reached; and one or more processors configured to provide a feedback signal based on a parameter for administering ACD CPR treatment to the patient's chest according to a desired treatment protocol.

31 Claims, 18 Drawing Sheets

Related U.S. Application Data continuation of application No. 15/720,837, filed on Sep. 29, 2017, now Pat. No. 11,052,019.

(60) Provisional application No. 62/402,688, filed on Sep. 30, 2016.

(52) U.S. Cl.
CPC .. *A61H 2031/001* (2013.01); *A61H 2031/002* (2013.01); *A61H 2201/5061* (2013.01); *A61H 2201/5064* (2013.01)

(58) Field of Classification Search
CPC ............ A61H 31/008; A61H 2031/001; A61H 2201/0127; A61H 2201/50; A61H 2201/5058; A61H 2201/5061
See application file for complete search history.

(56) References Cited

U.S. PATENT DOCUMENTS

| | | | |
|---|---|---|---|
| 11,052,019 B2 * | 7/2021 | Freeman | A61H 31/005 |
| 11,701,295 B2 * | 7/2023 | Freeman | A61H 31/005 128/205.24 |
| 2012/0330200 A1 | 12/2012 | Voss et al. | |
| 2013/0218056 A1 | 8/2013 | Aelen et al. | |
| 2014/0323928 A1 | 10/2014 | Johnson | |
| 2015/0045704 A1 | 2/2015 | Lurie et al. | |
| 2016/0136042 A1 | 5/2016 | Nilsson et al. | |
| 2017/0079876 A1 | 3/2017 | Freeman | |
| 2017/0105898 A1 | 4/2017 | Taylor et al. | |
| 2018/0021216 A1 | 1/2018 | Paradis | |
| 2019/0175443 A1 | 6/2019 | Hardig et al. | |

\* cited by examiner

ACTIVE COMPRESSION DECOMPRESSION CARDIOPULMONARY RESUSCITATION CHEST COMPRESSION FEEDBACK

RELATED APPLICATION

This application is a continuation application of U.S. Application Ser. No. 17/344,343, filed on Jun. 10, 2021, which is a continuation application of U.S. application Ser. No. 15/720,837, filed on Sep. 29, 2017, which claims priority to U.S. Provisional Patent Application No. 62/402,688 filed on Sep. 30, 2016, the entire content of which is hereby expressly incorporated by reference herein.

TECHNICAL FIELD

This document relates to cardiac resuscitation systems, and in particular to systems for assisting rescuers in performing and optimizing chest compressions performed in association with cardio-pulmonary resuscitation (CPR).

BACKGROUND

Acute care is delivered to patients in emergency situations in the pre-hospital and hospital settings for patients experiencing a variety of acute medical conditions involving the timely diagnosis and treatment of disease states that, left alone, will likely degenerate into a life-threatening condition and, potentially, death within a period of 72 hours or less. Stroke, dyspnea (difficulty breathing), traumatic arrest, myocardial infarction and cardiac arrest are a few examples of disease states for which acute care is delivered to patients in an emergency setting. Acute care comprises different treatment and/or diagnosis, depending upon the disease state. Cardiac arrest is one example that highlights critical interactions between the heart and the brain, and it remains a leading cause of death. Other examples include shock, traumatic brain injury, dehydration, kidney failure, congestive heart failure, wound healing, diabetes, stroke, respiratory failure, and orthostatic hypotension.

Despite advances in the field of circulatory enhancement, the need for improved approaches for treating patients with impaired circulation remains an important medical challenge. One example of acute care is cardio-pulmonary resuscitation (CPR), which is a process by which one or more acute care providers may attempt to resuscitate a patient who may have suffered an adverse cardiac event by taking one or more actions, for example, providing chest compressions and ventilation to the patient. Evidence indicates that promptly re-establishing systemic blood flow and thereby maintaining threshold levels of coronary and cerebral perfusion can increase the success of the CPR treatment.

Chest compressions are an important element of CPR during the first five to eight minutes after CPR efforts begin, because chest compressions help maintain circulation through the body, heart, and brain, which are the organs that can sustain substantial damage from an adverse cardiac event. Traditional chest compressions include two phases: one, which is referred to as the "active compression phase" where the chest is compressed by the direct application of external pressure and another one, which is referred to as the "relaxation phase" and occurs when pressure is withdrawn and the natural elasticity of the patient's chest wall causes expansion. The chest expansion of the relaxation phase serves to partially refill the cardiac chambers with blood. In conventional CPR, the air necessary for blood oxygenation is provided through periodic ventilation of the patient.

Generally, American Heart Association CPR Guidelines define protocols, by which a rescuer is to apply the chest compressions in coordination with ventilations. For example, 2015 AHA Guidelines specify a ratio of 30:2 for compressions to ventilations (e.g., thirty compressions for every two breaths) and compressions are to be performed at a rate of between 100 and 120 per minute.

SUMMARY

This document describes systems and techniques that can be used to help manage a cardiopulmonary resuscitation (CPR) treatment to a patient in need of emergency assistance. In one implementation, a system includes: an applicator device configured to provide active compression decompression (ACD) therapy to a patient's chest, at least one sensor configured to be coupled to the patient's chest and to measure at least one parameter related to the ACD CPR treatment, and one or more processors configured to perform a plurality of operations. The operations include processing the at least one parameter related to the ACD CPR treatment, determining the phase of the ACD CPR treatment and whether at least one transition point in the ACD CPR treatment has been reached, and generating a feedback signal based on the determination, wherein the feedback signal is selected according to a predetermined treatment protocol.

In another implementation, a system includes: an applicator device configured to provide the ACD CPR treatment to a patient's chest according to a plurality of phases, the phases comprising at least an elevated compression phase, a non-elevated compression phase, an elevated decompression phase, and a non-elevated decompression phase, at least one sensor configured to be coupled to the patient's chest and to measure at least one parameter related to the ACD CPR treatment, and one or more processors configured to perform a plurality of operations. The operations include processing the at least one parameter related to the ACD CPR treatment, determining the phase of the ACD CPR treatment based on the information for determining whether at least one transition point has been reached, the at least one transition point including a transition between an elevated position above a neutral point and a non-elevated position below the neutral point, and providing a feedback signal based on the at least one parameter for administering ACD CPR treatment to the patient's chest according to a desired treatment protocol.

In some aspects, the at least one sensor includes at least one of a motion sensor and a force sensor. The motion sensor can measure the at least one parameter related to the ACD CPR treatment. The force sensor can measure the at least one parameter related to the ACD CPR treatment. The motion sensor can measure the information for determining whether at least one transition point of the ACD CPR treatment has been reached. The motion sensor can include one or more accelerometers configured to detect an acceleration signal associated with the displacement of the at least the portion of the patient's chest. A first accelerometer can be configured to detect an acceleration signal associated with displacement of a first portion of the patient's chest and a second accelerometer can be configured to detect an acceleration signal associated with displacement of a second portion of the patient's chest.

In other aspects, the information for determining whether the at least one transition point has been reached can include at least one of displacement information and force information. The at least one transition point can include a transition point between an elevated position above a neutral point and a non-elevated position below the neutral point. The transition point can be between a non-elevated decompression phase and an elevated decompression phase. The feedback signal can include providing a prompt to maintain a desired release velocity during decompression upstroke for providing a negative intrathoracic pressure according to the desired treatment protocol.

In yet another aspect, the prompt to maintain the desired release velocity can include at least one of an audio prompt, a verbal prompt, a non-verbal prompt, a visual prompt, a graphical prompt and a haptic prompt. The prompt to maintain the desired release velocity can include a signal for operating an automated compressor. The feedback signal can include providing a prompt to limit a force applied to the patient's chest during decompression upstroke for reducing risk of injury according to the desired treatment protocol. The prompt to limit a force applied to the patient's chest during decompression upstroke can include at least one of an audio prompt, a verbal prompt, a non-verbal prompt, a visual prompt, a graphical prompt and a haptic prompt. The prompt to limit a force applied to the patient's chest during decompression upstroke can include a signal for operating an automated compressor.

In yet another aspect, the transition point can be between an elevated compression phase and a non-elevated compression phase. The at least one transition point can include a transition point between an elevated decompression phase and an elevated compression phase. The transition point can be between an elevated decompression phase and a hold time above a neutral point. The transition point can be between a hold time above the neutral point and an elevated compression phase. The hold time can be between about 50-200 milliseconds. The hold time can be sufficient to promote net blood flow to the heart of the patient.

In yet another aspect, the feedback signal can include providing a prompt to maintain at least one of a compression depth and a compression rate according to the desired treatment protocol. The prompt to maintain at least one of a compression depth and a compression rate can include at least one of an audio prompt, a verbal prompt, a non-verbal prompt, a visual prompt, a graphical prompt and a haptic prompt. The prompt to maintain at least one of a compression depth and a compression rate can include a signal for operating an automated compressor. The feedback signal can include providing information regarding at least one of a displacement above the neutral point and a depth of compression below the neutral point.

In yet another aspect, the at least one transition point can include a transition point between a non-elevated compression phase and a non-elevated decompression phase. The transition point can be between a non-elevated compression phase and a hold time below the neutral point. The transition point can be between hold time below the neutral point and a non-elevated decompression phase. The hold time can be between about 50-200 milliseconds. The hold time can be sufficient to promote net blood flow to the head of the patient. The feedback signal can include providing a prompt to ventilate during decompression upstroke. The prompt to ventilate can include at least one of an audio prompt, a verbal prompt, a non-verbal prompt, a visual prompt, a graphical prompt and a haptic prompt. The prompt to ventilate can include a signal for operating an automated ventilator.

In yet another aspect, the feedback signal can include providing a prompt to maintain a sufficient release velocity during decompression upstroke for providing a negative intrathoracic pressure according to the desired treatment protocol. The at least one parameter related to the ACD CPR treatment can include at least one of displacement, velocity, acceleration, time, work, power, pressure, direction and orientation. The feedback signal can include providing a prompt to maintain the applicator device according to a desired orientation during application of the ACD CPR treatment.

In yet another aspect, the system can include a user interface configured to assist the rescuer interacting with the applicator device for providing ACD CPR treatment to the patient's chest. The user interface can be configured for displaying information representing effectiveness of CPR chest compressions. The user interface can be configured for displaying an indication of the phase of the ACD CPR treatment. The user interface can be configured to be displayed on a device external to the system (e.g., smartphone, smartwatch, tablet device, monitor, diagnostic device, or defibrillator). The applicator device can include one or more accelerometers configured to detect an acceleration signal associated with displacement of the applicator device. The system can include an adhesive pad configured to be adhered to at least a portion of a patient's chest.

In another implementation, a system for managing CPR treatment to a patient in need of emergency assistance by a rescuer can include: a chest decompression monitor configured to be adhered to and to detect a displacement of at least a portion of a patient's chest, an applicator device that can be configured to be releasable coupled to the chest decompression monitor and can be configured to generate a decompression force to be applied to the at least the portion of the patient's chest, and one or more processors configured to process the displacement and to provide a feedback associated with the decompression force.

In one aspect, the applicator device can include a motor for driving the applicator device to generate the decompression force. The system can include an automated controller for operating the motor, the automated controller being programmed to control the decompression force in response to the feedback provided by the one or more processors. The system can include a user interface configured to assist the rescuer interacting with the applicator device by providing instructions to generate the decompression force. The user interface being configured for displaying information representing effectiveness of CPR chest compressions. The user interface can be configured for displaying a compression non-elevated depth. The user interface can be configured for displaying a decompression elevated height. The user interface can be configured for displaying a trend graph representing chest remodeling. The user interface can be configured to be displayed on a device external to the system. The device external to the system can include at least one of a smartphone, a smartwatch, or a tablet device.

In other aspects, the chest decompression monitor can include one or more accelerometers configured to detect an acceleration signal associated with the displacement of the at least the portion of the patient's chest. The one or more processors are configured to process the acceleration signal to determine one or more of a velocity, an upstroke and a release time. A first accelerometer can be configured to detect the acceleration signal associated with the displacement of a left portion of the patient's chest and a second accelerometer can be configured to detect the acceleration signal associated with the displacement of a right portion of the patient's chest. The applicator device can include one or more accelerometers configured to detect an acceleration signal associated with the displacement of the applicator device. The system can include a sensor configured to measure a trans-thoracic impedance of the patient. The system can include a sensor configured to measure a tracheal pressure of the patient.

In another implementation, a system for applying guided active compression-decompression cardiopulmonary resuscitation to a patient in need thereof can include: an adhesive pad configured to be adhered to at least a portion of a patient's chest, an applicator device coupled to the adhesive pad and can be configured to generate a force to be applied to the at least the portion of the patient's chest, a sensor configured to monitor a signal of the at least the portion of the patient's chest in response to the force applied by the applicator device, and one or more processors configured to process the signal and to identify a phase of the ACD cardiopulmonary resuscitation.

In one aspect, the phase can be one of a non-elevated compression, a non-elevated decompression, an elevated decompression, and an elevated compression phases.

The one or more processors are configured to perform a calibration based on the identification of the phase. The one or more processors are configured to generate feedback based on the motion signal and the phase. The feedback can include at least one of a depth, a force or pressure amplitude, a force direction, a velocity, a compliance, a power, a release time, a displacement limit and a trans-thoracic impedance of the patient.

In another implementation, a system for applying guided ACD cardiopulmonary resuscitation to a patient in need thereof, can include: an adhesive pad configured to be adhered to at least a portion of a patient's chest, an applicator device coupled to the adhesive pad and can be configured to generate a decompression force to be applied to the at least the portion of the patient's chest, a sensor configured to monitor a fluid displacement in the patient in response to the decompression force applied by the applicator device, and one or more processors configured to provide a feedback based on the fluid displacement.

In some aspects, the system can include a valve to control the fluid displacement in response to the feedback. The sensor can be attached to a ventilation bag and can be configured to monitor air flow through the ventilation bag. The sensor can be configured to monitor a venous return in the patient. The sensor can be configured to monitor a tracheal pressure of the patient.

In other aspects, the system can include one or more motion sensors. The one or more motion sensors are included in the chest decompression monitor and are configured to detect an acceleration signal associated with the displacement of the at least the portion of the patient's chest. A first motion sensor can be configured to detect the acceleration signal associated with the displacement of a left portion of the patient's chest and a second accelerometer can be configured to detect the acceleration signal associated with the displacement of a right portion of the patient's chest. The one or more motion sensors are included in the applicator device and are configured to detect an acceleration signal associated with the displacement of the applicator device.

Other features and advantages will be apparent from the description, from the drawings, and from the claims.

DETAILED DESCRIPTION

Figure 1:
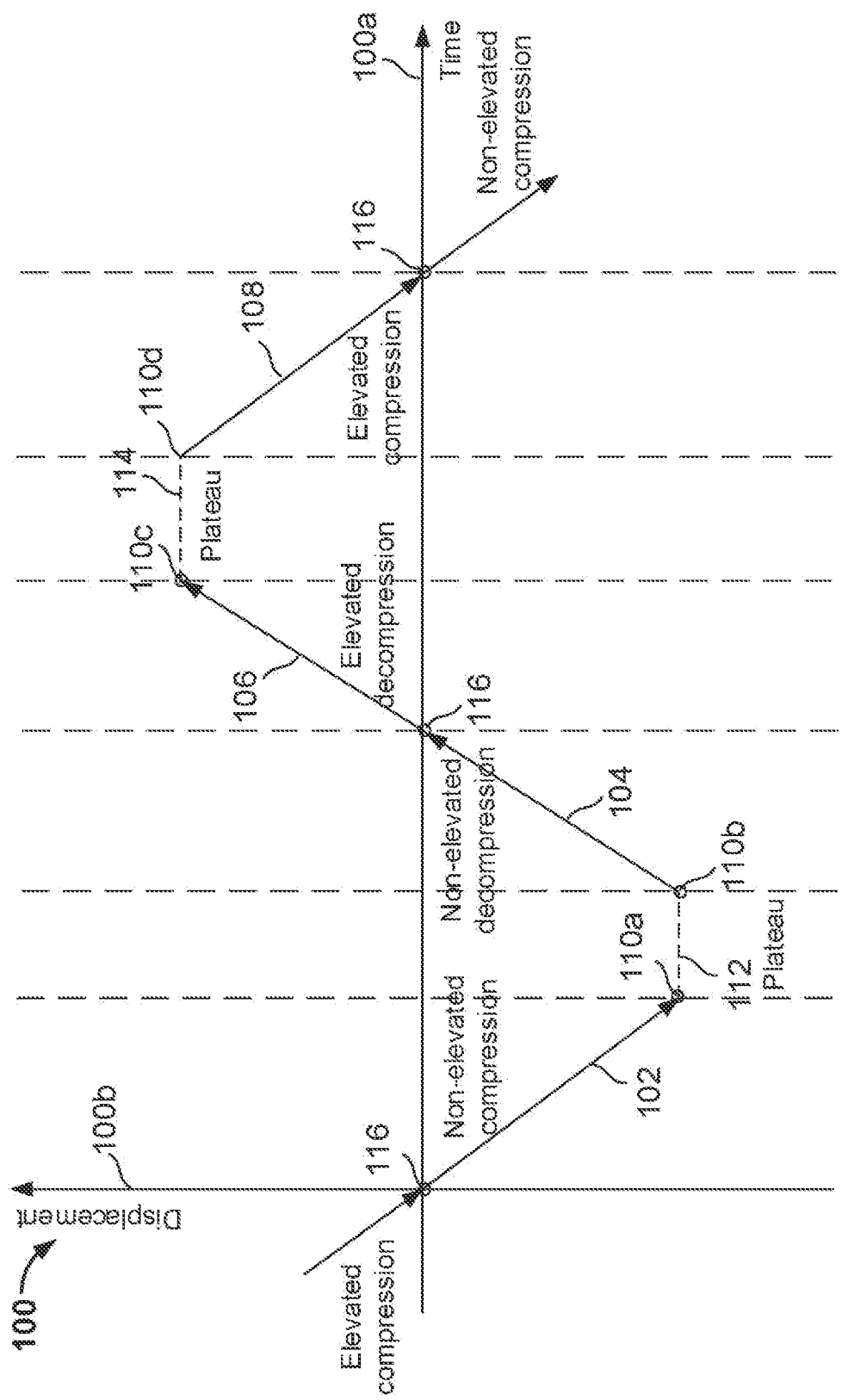
FIG. 1 shows an example graph including temporal variation of an example of a signal indicative of ACD CPR chest compression treatment.

Implementations of the present disclosure are generally directed to systems for managing a cardiopulmonary resuscitation (CPR) treatment to a patient in need of emergency assistance, such as a patient suffering of cardiac arrest. In particular, implementations of the present disclosure are generally directed to systems for assisting a rescuer to perform active compression decompression (ACD) CPR chest compressions. ACD CPR differs from standard CPR chest compressions in that the patient's chest is actively pressed and lifted in an alternating manner. An exemplary device to assist in the performance of ACD CPR is the RESQPUMP® (provided by ZOLL Medical). Such devices have the ability to couple to the patient's chest to facilitate lifting of the chest during the decompression phase. By actively lifting the chest, the negative intrathoracic pressure is increased causing more venous blood to flow to the heart and lungs during the decompression phase. Thus, in addition to compression of the chest to improve blood flow from the heart to peripheral tissues of the body, decompression of the chest offered through ACD reduces intrathoracic pressure, resulting in enhanced venous return of blood from peripheral tissues back to the heart and refilling of the cardiac chambers. ACD treatment involves a number of different phases that each have respective effects on the body. Referring to FIG. 1, standard CPR (S-CPR) chest compressions do not have the ability to actively decompress the chest during the decompression phase, and therefore, for S-CPR, the expansion of the chest is based solely on the natural elasticity of the patient's chest wall. With S-CPR, upon release of compression forces on the sternum, there is no external decompressive force on the sternum exerted by the rescuer, and so is only composed of the non-elevated compression and non-elevated decompression phases. On the other hand, ACD CPR actively re-expands (decompresses) the chest, and therefore may be composed of both elevated compression and decompression phases and non-elevated compression and decompression phases.

The example graph 1 includes a temporal (X) axis 100*a* and a displacement (Y) axis 100*b*. The neutral position 116 is the displacement at which zero static compression or decompression force is exerted by the rescuer on to the patient during compressions. The example graph 100 includes a plurality of neutral points 116 and other phase transition points 110*a*, 110*b*, 110*c*, and 110*d*. Accordingly, the feedback provided to a user or system providing ACD treatment to a patient may vary depending on the particular phase of ACD such that the feedback can be a phase-specific feedback. The phase-specific feedback signal can be selected according to a predetermined treatment protocol. For performing an ACD CPR chest compression treatment, a rescuer can attach the system for managing ACD CPR chest compression treatment to a patient's chest and apply force on a handle of the system during multiple phases of ACD CPR chest compression treatment.

Figure 2:
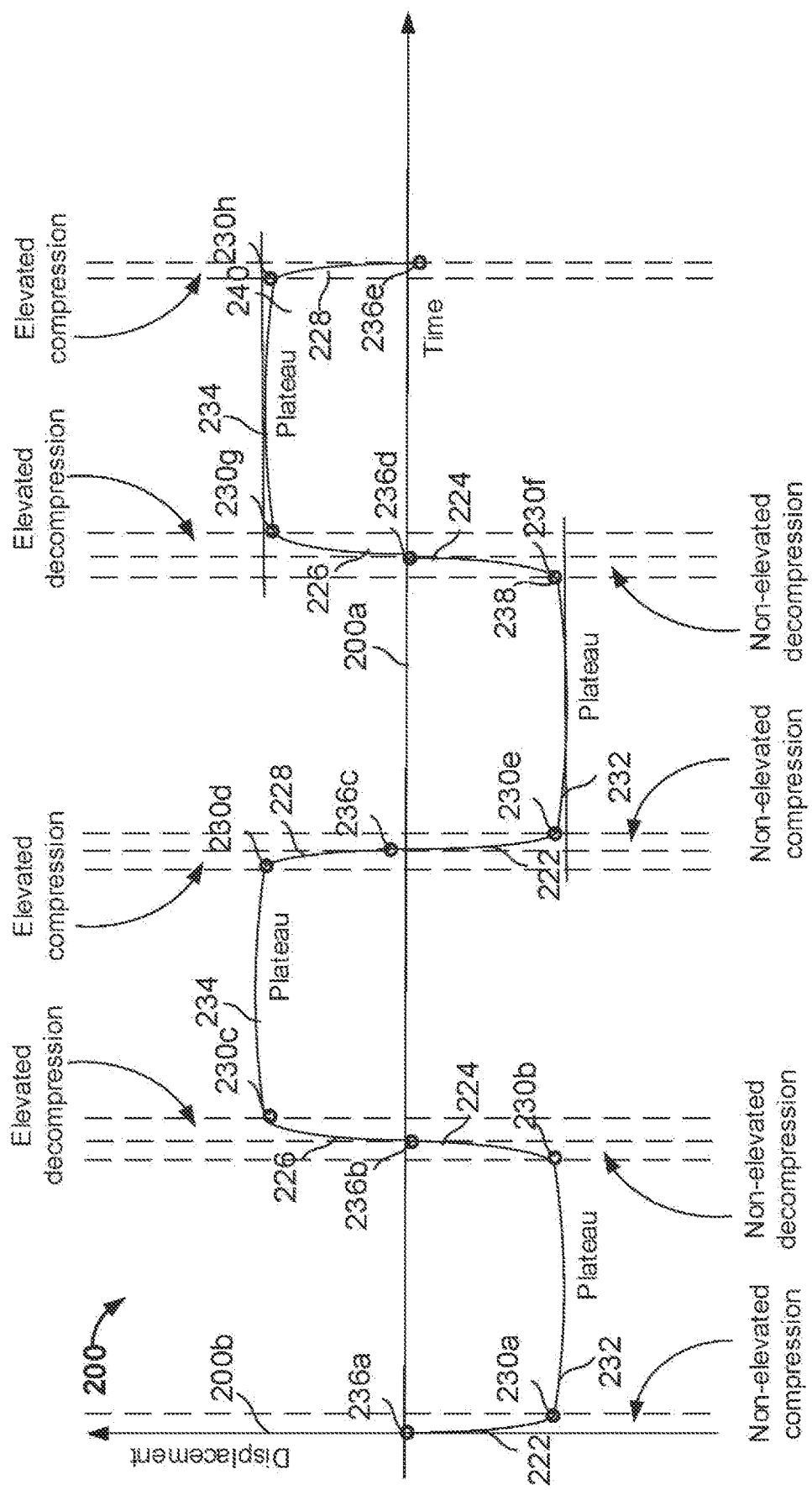
FIG. 2 shows another example graph including temporal variation of an example of a signal indicative of ACD CPR chest compression treatment.

It is desirable for the phases of ACD CPR chest compression treatment to be analyzed and distinguished from one another so that phase-specific feedback can be provided and the rescuer can optimize delivery of the compression and decompression for maximal therapeutic benefit. Referring to FIGS. 1 and 2, these phases may include at least one of an elevated compression, non-elevated compression, non-elevated decompression, and elevated decompression phases. If the phases can be identified, feedback can be provided to a rescuer that directs the rescuer to perform chest compressions that are likely to be more effective at resuscitating the patient and less likely to lead to injury. For example, feedback could be provided directing the rescuer to maintain release velocity during upstroke and optionally hold (pause) above a neutral point of chest compression, which may have a tendency to enhance blood flow back into the heart. As another example, feedback could be provided directing the rescuer to hold (pause) below the neutral point of chest compression, which may have a tendency to enhance blood flow to the head, resulting in a greater likelihood of neurologically intact survival.

FIG. 1 illustrates an example graph 100 including temporal variation of an example of a signal indicative of ACD CPR chest compression treatment. In some implementations, the example graph 100 corresponds to a sternal displacement as determined from a motion sensor such as an accelerometer as described below with reference to FIGS. 3 and 4, such as a signal depicting the force applied to the chest of a patient or the displacement of the patient's chest during ACD CPR chest compression treatment. In some implementations, data corresponding to the graph 100 would be calculated by a computer system, e.g., one or more computer processors of a defibrillator (e.g., the defibrillator 312 shown in FIG. 3) or an ACD device (e.g., the ACD device 408 shown in FIG. 4) or another kind of computer system (e.g., the computer system 310 shown in FIG. 3).

The neutral position location 116 or other phase transition points may be determined using techniques for instance as described in "Chest Compliance Directed Chest Compressions", filed on Sep. 16, 2016 as U.S. patent application Ser. No. 15/267,255 and published as U.S. Patent Publication No. 2017-0079876, and is incorporated by reference herein in its entirety. In some examples, the neutral position may be determined based on data such as an estimated depth of chest compression and an estimate of chest compliance. For example, when a victim's chest is at a neutral position of chest compression (generally corresponding to the natural resting position of the chest), chest compliance tends to be at its highest point. This may be determined, e.g., using a point of intersection of a hysteresis compliance curve, because the point of intersection tends to correspond to a neutral position of chest compression.

The neutral position 116 may be identified as the position at which zero force or pressure is exerted by the rescuer during ACD compressions and the spatial variation transitions from a negative value to a positive value or from a positive value to a negative value. Because of so-called chest remodeling that occurs during chest compressions, this zero-force neutral position 116 may change over the course of resuscitation efforts, as the anterior/posterior diameter of the patient will decrease after multiple compression cycles. Alternatively, the neutral position location 116 may be simply the initial position of the sternum prior to initiation of chest compressions.

The example graph 100 illustrates the phases of the ACD CPR chest compression treatment: a non-elevated compression phase 102, a non-elevated decompression phase 104, an elevated decompression phase 106, and an elevated compression phase 108. The non-elevated compression phase 102 corresponds to the time interval during which a rescuer is actively compressing the patient's chest as a downstroke from a neutral level to a particular compression depth. The non-elevated decompression phase 104 corresponds to the time interval during which a rescuer is decompressing the patient's chest as an upstroke from a particular compression depth to a neutral level. The non-elevated decompression phase 104 may or may not be active in nature. That is, the acute care provider may actively pull up on the patient's chest at an upward velocity faster than the natural velocity of chest wall recoil, enhancing the overall effects of chest wall recoil (e.g., increasing negative intrathoracic pressure). Or, the acute care provider may pull up or reduce the applied force in a manner that allows the patient's chest to undergo natural recoil. Here, the release velocity may be the same as or slower than the natural recoil velocity of the chest.

The elevated decompression phase 106 corresponds to the time interval during which a rescuer is actively decompressing the patient's chest. This active decompression may occur during either the non-elevated or elevated decompression phases 104, 106. Active decompression involves pulling upward of the chest wall to further enhance negative intrathoracic pressure. The elevated compression phase 108 corresponds to the time interval during which a rescuer is compressing the patient's chest from a particular decompression amplitude to the neutral level. The elevated compression phase 108 may or may not be active in nature. For instance, the acute care provider may let go or otherwise release the patient's chest to allow the chest to naturally rebound. Or, the acute care provider may actively push down on the patient's chest at a downward force that causes the chest to return back to its natural state faster than would otherwise be the case if the chest was simply let go. Transition points 110*a*, 110*b*, 110*c*, and 110*d* define the point corresponding to the end of a phase and the beginning of another phase of the ACD chest compression treatment.

In some implementations, the transition between elevated and non-elevated phases can correspond to the neutral points 116 of the patient's chest wall (e.g., the level at which the chest wall would be if ACD CPR chest compression treatment would not be applied, which can be measured before the initiation of the ACD CPR chest compression treatment). Transition points 110a, 110b, 110c, and 110d can be between compression and decompression phases, or between either compression or decompression and plateau phases.

In some implementations, the transition points 110a, 110b, 110c, and 110d can be detected by a transition point detector based on a threshold. Such a transition point detector may be part of the system, taking one or more inputs from the sensor(s) associated with the ACD device, and determining from the input(s) whether a transition has occurred between phases of ACD CPR treatment. The particular type of feedback provided to the rescuer may be selected and suitably presented to the rescuer, based on the detection of a transition from one phase to another. For example, each ACD CPR treatment is associated with a compression range between a maximum compression and a maximum decompression. The maximum compression and decompression values can be preset values stored in a database. The maximum compression value can be associated with a transition point 110a and/or 110b. The maximum decompression can be associated with a transition point 110c and/or 110d. The transition points can be associated with maximum compression or decompression based on a comparison of chest displacement at increments of time (e.g., every millisecond) represented as variation along displacement axis 100b relative to the time axis 100a.

An ACD CPR chest compression treatment template can define the spatio-temporal path of the compression treatment, such as example graph 100, from the neutral point 116 to the first transition point 110a without exceeding a first threshold (e.g., a desired maximum compression value) and from the neutral point 116 to the following transition point 110c without exceeding a second threshold (e.g., a desired maximum decompression value). In some implementations, the scalar value of the first threshold can be different than the scalar value of the second threshold. Further, each of the first threshold and the second threshold can be selected based on one or more physiological characteristics (e.g., chest compliance).

In some implementations, the threshold values are preset values, which may be selected based on chest compliance. For example, the threshold values can depend on one or more physical characteristics (e.g., size, weight, and other physical measurements/records) of a patient. The threshold values can be calculated prior to the ACD CPR chest compression treatment or they can be retrieved from a stored medical file based on patient's characteristics. In some implementations, the threshold values can be used to control the transition between multiple phases of the ACD CPR chest compression treatment, such that limiting the decompression force above neutral point 116 can lessen the risk of rib fracture.

For example, a threshold detector can monitor the spatio-temporal path of the compression treatment, such as example graph 100, and in response to detecting a transition point 110a of a non-elevated compression it can trigger the initiation of the following phase, such as a non-elevated plateau phase 112 or a non-elevated decompression phase 104. The monitoring of the spatio-temporal path can be based, for instance, on data provided by a motion sensor such as an accelerometer, positioned at the location of the chest wall at which ACD therapy is delivered. In such a case, the acceleration data may be single- and double-integrated to determine the displacement as well as the change in displacement of the chest wall. Accordingly, during the non-elevated compression phase 102, a transition point 110a may be detected when the change in displacement of the chest wall during downstroke is reduced by a threshold amount (e.g., change in displacement reduced to less than 20%, less than 10%, etc.). The transition point 110b may be further determined when the change in displacement shifts in an opposite direction so as to detect the decompression upstroke. For example, the transition point 110b may be detected when the change in displacement of the chest wall is increased by a threshold amount (e.g., change in displacement increased by more than 50%, more than 60%, more than 70%, more than 80%, etc.). Accordingly, as discussed herein, where the type of feedback selected and presented during non-elevated compression 102 may be related to chest compression depth/rate, upon transitioning to non-elevated decompression 104, the type of feedback selected and presented may be related to release velocity.

In some implementations, the example graph 100 includes one or more plateau phases, such as a non-elevated plateau phase 112 and an elevated plateau phase 114. In some examples, the detector may determine that a plateau phase has been reached if the displacement of the chest wall remains substantially constant and/or the change in displacement is minimal. The plateau phases 112 and 114 can correspond to a hold time. The hold time can be included in the ACD CPR chest compression treatment, for example, to help improve vascularization and oxygenation. For example, holding a non-elevated plateau phase 112 for a suitable period of time can be sufficient to promote net blood flow to the head of the patient by overcoming inertia that may normally be present within the vasculature. For example, holding an elevated plateau phase 114 for a suitable period of time can be sufficient to promote net blood flow to the heart of the patient (e.g., to enhance venous return and refilling of the cardiac chambers). The hold time corresponding to the non-elevated plateau phase 112 and/or the elevated plateau phase 114 can be between about 10-1000 milliseconds, between about 10-500 milliseconds, between about 10-200 milliseconds, between about 50-200 milliseconds, between about 200-500 milliseconds, or a period of time falling within another suitable range.

During elevated compression and non-elevated compression, a rescuer can press downwardly on a handle of the system with sufficient force to compress the patient's chest from a level above a neutral point of the chest wall to a level below the neutral point. This action induces arterial blood circulation by ejecting blood from cardiac chambers toward peripheral tissues. As discussed herein, the type of feedback provided during non-elevated compression may include chest compression depth and chest compression rate.

On the other hand, during non-elevated decompression and elevated decompression phases of ACD CPR, the rescuer can pull upwardly on the handle of the system to actively expand the patient's chest. Actively shifting the position of the chest wall from that which would be achieved by the natural recoil of the chest wall enhances refill of blood back into the cardiac chambers and, in some cases, may further assist in brining air into the patient's lungs in a more efficient manner. As discussed herein, the type of feedback provided during non-elevated decompression and elevated decompression may include release velocity. The feedback provided during elevated decompression may further include force along with release velocity. This is because overly excessive decompression force on the chest of the patient, particularly during the elevated decompression phase may lead to injury. Accordingly, the ACD device may include one or more force sensors, 532, 533, that provide an indication to the system of how much force is applied by the rescuer. Once a threshold level of force is reached, the system may inform the rescuer that the decompression force is too high. During the decompression phase (non-elevated and elevated), while it may be desirable to reach a sufficient release velocity to beneficially generate a reduced level of intrathoracic pressure, the force applied to the chest in efforts to achieve such release velocities should not be so vigorous such that excessive levels that would result in harm to the patient are achieved.

In some versions of the system, feedback may be provided on measurements of some feature of the non-elevated compression phase 102 and the elevated decompression phase 106. As noted, in some cases, the feedback feature for the non-elevated compression phase may be the compression depth, and the feature of the elevated decompression phase 106 may be some force or pressure measurement occurring during the elevated decompression (ED) phase 106. The force or pressure measurement during the ED phase may be an average, peak, median, RMS, or other mathematical characterization of the force or pressure, and compared to a set of desired levels to result in favorable patient outcomes. For example, as discussed above, the system may provide feedback such that the force/pressure during the ED phase is not overly excessive. Accordingly, if a certain threshold level of force is reached during the ED phase, the system may alert the user that excessive levels of force have been reached. Such threshold levels may be set according to patient characteristics, or default values may be provided. In some embodiments, the maximum threshold force values may be between approximately 10-30 kg, between approximately 10-15 kg.

Each of the phases of the ACD chest compression cycle can be monitored for one or more compression cycle and feedback provided so that the rescuer can optimize delivery of the compression and decompression for maximal therapeutic benefit. For example, the compression magnitude can be in a range from about 3.5 cm to about 5 cm for the non-elevated compression phase 102 and the compression rate can be in a range from about 60 compressions to about 150 compressions per minute. In certain embodiments, the recommended compression rate for ACD therapy may be approximately 80 compressions per minute.

FIG. 2 illustrates another example graph 200 including temporal variation of an example of a signal indicative of ACD CPR chest compression treatment. As compared to FIG. 1, the example graph 200 FIG. 2 illustrates longer periods of the plateau phases and reduced decompression phases 224 and 226 and compression phases 228 and 222. The example graph 200 could be performed through real-time feedback controlled treatment. The example graph 200 includes a temporal axis 200*a* and a displacement axis 200*b*, the intersection of which marks the neutral point 236 of the patient's chest. The transition points 230*a*-230*j* define the transitions between elevated and non-elevated phases of the ACD CPR chest compression treatment. In some implementations, some transition points (e.g., transition point 230*c*) can correspond to the neutral point 236 of the patient's chest wall (e.g., the level at which the chest wall would be if ACD CPR chest compression treatment would not be applied, which can be measured before the initiation of the ACD CPR chest compression treatment). Some transition points (e.g., transition points 230*a*, 230*b*, 230*c*, 230*d*, 230*e*, 230*f*, 230*g*, 230*h*) can be above or below the neutral point 236*a*, 236*b*, 236*c*, 236*d*, 236*e* of the patient's chest wall.

In some implementations, the example graph 200 includes one or more plateau phases, such as a non-elevated plateau phase 232 and an elevated plateau phase 234. The plateau phases can correspond to a time of approximately constant compression and decompression force, respectively. The approximately constant force time can be included in the ACD CPR chest compression treatment to improve vascularization and oxygenation. The transition from a non-elevated compression or elevated decompression to a plateau phase can be a smooth transition, such that the variation of the compression or decompression force and/or displacement relative to time is gradually decreasing until the force or displacement remains approximately constant over a preset time. The preset time can be selected based on one or more physiological parameters. The preset time of a non-elevated plateau phase 232 can be sufficient to promote net blood flow to the head of the patient. The preset time of an elevated plateau phase 234 can be sufficient to promote net blood flow to the heart of the patient. The preset time corresponding to the non-elevated plateau phase 232 and/or the elevated plateau phase 234 can be between about 50-200 milliseconds.

In some implementations, the rescuer is guided into performing a smooth transition from an active compression or decompression to a plateau phase (e.g., corresponding to an exponential variation in the applied force until it reaches a particular compression threshold 238 and/or depression threshold 240). The compression threshold 238 and/or decompression threshold 240 can be selected based on physiological characteristics of the patient and/or ACD CPR chest compression requirements.

For example, the feedback provided to limit the decompression force above the neutral point below the depression threshold 240 can be configured to decrease the risk of rib fracture in a patient with a particular body structure. In some embodiments, the elevated decompression phase 226 and the elevated plateau phase 234 can be synchronized with patient's ventilation. Alternatively, the patient's ventilation can be synchronized to occur during both the non-elevated decompression and elevated decompression phases (i.e. substantially the whole of the decompression phase) as ventilation will be more efficient and safer when the ventilation occurs when the intrathoracic pressure is negative such as during the decompression phase. In some versions, the synchronization may be accomplished based on feedback provided to the rescuer such as a prompt that indicates when a ventilation is to start and stop. That is, when a transition point is detected such that the system determines that non-elevated decompression is beginning, the system may provide a prompt to a user and/or machine to initiate a positive pressure ventilation breath. For example, the synchronization may be accomplished based on an output to a mechanical ventilation unit that indicates which of the phases an inspiratory ventilation cycle can occur.

Figure 3:
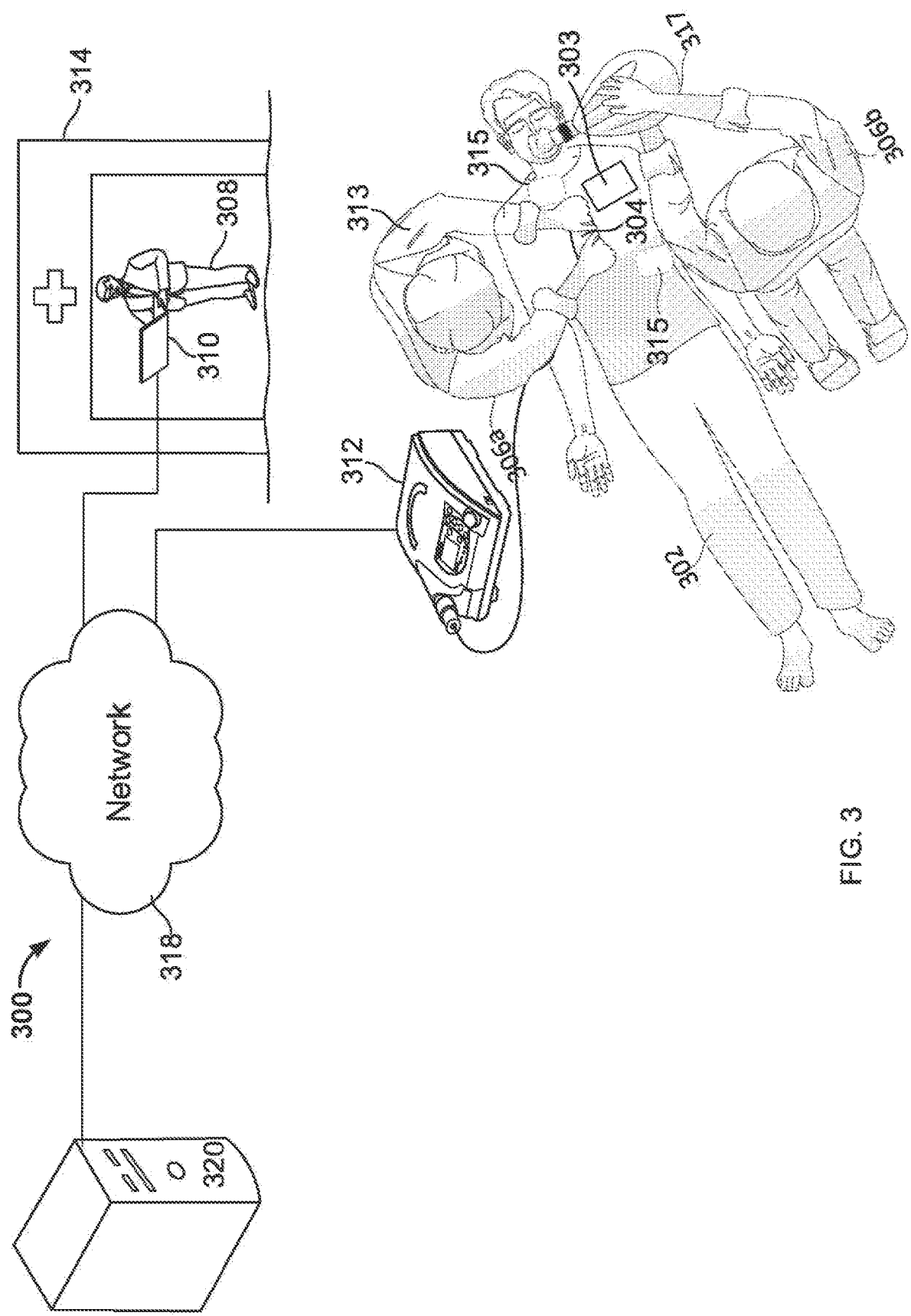
FIG. 3 shows an overhead view of rescuers providing resuscitative treatment to a patient using a CPR chest compression assistance system in accordance with an embodiment.

FIG. 3 shows an example of a system 300 for responding to an emergency medical condition of a patient 302 by providing CPR chest compression. FIG. 3 illustrates an overhead view of rescuers 306*a* and 306*b* performing CPR chest compression on the patient 302 using an ACD CPR chest compression system 304. In the illustrated example of FIG. 3, the rescuers 306*a* and 306*b* are already in position and providing care to the patient 302, with rescuer 306*a* in position and providing chest compressions to the torso of the patient 302 by using ACD CPR chest compression system 304, and rescuer 306*b* providing ventilation using a ventilation bag 307. In some implementations, the configuration and geometry of the ACD CPR chest compression system 304 enables the rescuer 306a to use the same body position and compression technique as in standard CPR chest compression. In some implementations, the ACD CPR chest compression system 304 is configured to enable the rescuer 306a to perform active chest decompression by maintaining a firm grip on the ACD CPR chest compression system 304 and swinging the body weight upwards after compression. Motion sensors and/or pressure/force sensors may be included in the housing of the handle or piston of the ACD CPR chest compression system 304, as further described with reference to FIGS. 5A and 5B.

Figure 5A:
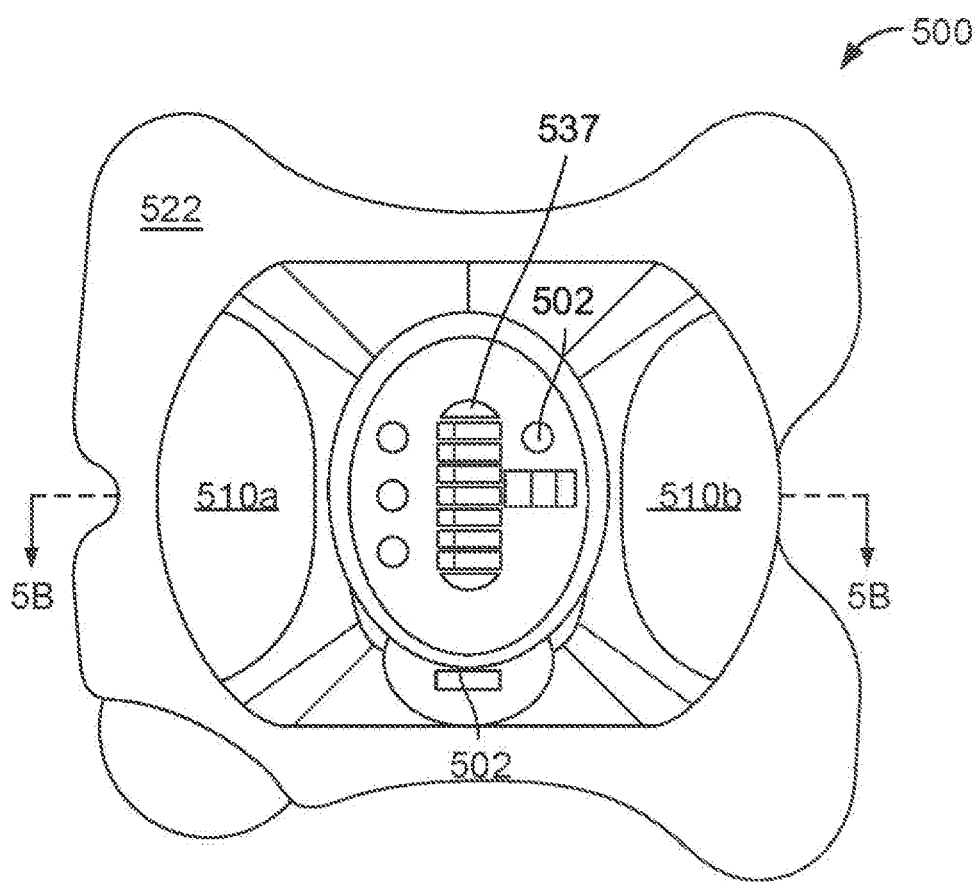
FIGS. 5A and 5B show top and cross-sectional views of an example ACD device in accordance with an embodiment.
Figure 5B:
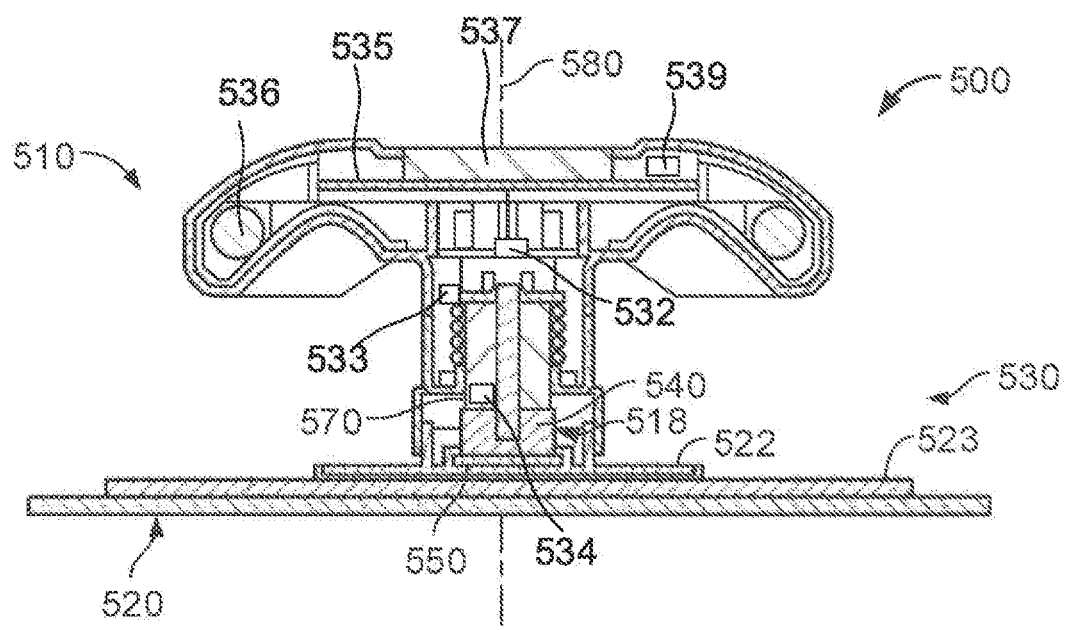

Feedback may be provided on the elevated decompression phase 26, for instance, providing and indicator of the amount of force delivered to the patient's chest by the ACD device during the elevated decompression phase 26, as measured by a decompression force sensor 532, as shown in FIG. 5B. The decompression force sensor may be configured as a compression sensor such as a load cell (e.g. LBMU Ultra Compression Load Button, Interface Advanced Force measurement, Scottsdale AZ) with a load arm 534 that engages with the load cell during decompression. There may also be one or more separate compression force/pressure sensors 533 to measure the downward force or pressure during the compression phases (e.g. elevated compression, non-elevated compression, and non-elevated decompression).

Referring to FIG. 5B, sensors such as force sensors 532, 533 are included in the housing for measuring the pressures and forces during the various phases. Motion sensors such as an accelerometer, gyroscope, etc. may also be located in the housing for measuring the motion of the patient's sternum during chest compressions, for instance accelerometer 534 located at the distal end of the system piston 570, or the motion sensor can be located in the handle, e.g. a motion sensor that may be a tilt and off-axis motion sensor 539 that can measure if the rescuer is properly directing the force and motion vector of the compression and decompression so that therapy is properly being delivered to the patient. For instance, it may be preferable for the direction in which compression and decompression therapy is administered to be substantially perpendicular to the sternum of the patient, rather than at an angle which may otherwise lead to less effective or otherwise inefficient treatment. Sensors may be powered for example by battery 536 and power supply located on circuit board 535, and outputs of the sensors are amplified and signal conditioned using techniques known to those skilled in the art then digitized by A to D converters and processed by a microprocessor to output measurements of the various phases of the compression cycle. The force and motion sensors may also be located in the defibrillation electrodes 204 connected to a defibrillator 312.

Referring back to FIG. 3, the rescuers 306a and 306b can be lay rescuers who were in the vicinity of the patient 302 when the patient 302 required care, or can be trained medical personnel, such as emergency medical personnel (EMTs). Although two rescuers are shown in FIG. 3, additional rescuers can also care for the patient 302, and can be included in a rotation of rescuers providing particular components of care to the patient 302, where the components can include chest compressions, ventilation, administration of drugs, and other provisions of care.

In general, the system 300 includes various portable devices for monitoring on-site care given to the patient 302. The various devices can be provided by emergency medical personnel who arrive at the scene and who provide care for the patient 302, such as rescuers 306a and 306b. The onsite rescuers 306a and 306b can be assisted by remote medical personnel 308, located at a medical facility 314 within a healthcare network. In the illustrated example, the rescuers 306a and 306b use several devices to provide an emergency treatment to the patient 302.

The devices used by the rescuers 306a, 306b, and/or the medical personnel 308 during CPR chest compression can include the ACD CPR chest compression system 304 and a portable defibrillator 312. A visual metronome can guide the rescuer 306a to perform each phase of ACD CPR chest compression treatment at the appropriate rate and force. The ACD CPR chest compression system 304 can be a stand-alone device that is placed on the patient's chest (as illustrated in FIG. 3). The ACD CPR chest compression system 304 can also be attached to another device used by the medical personnel during CPR chest compression, such as the portable defibrillator 312. The attachment of the ACD CPR chest compression system 304 with other devices can enable synchronization of multiple CPR-related procedures (e.g. ventilations, defibrillation, etc.).

In addition to the ACD CPR chest compression system 304, FIG. 3 shows a portable defibrillator 312 and ancillary components arranged to provide feedback and instruction to rescuers 306a and 306b. FIG. 3 shows an example in which visual feedback can be provided to the rescuer 306a from a location that is away from the defibrillator unit, and more immediately in the line of sight and focus of attention of the rescuer 306a, such as a graphical user interface of a local feedback display on the ACD CPR chest compression system. Referring to FIG. 5A, the local feedback display 537 may take the form of a bar graph, or provide more sophisticated information via a graphical display such as an LCD containing information such as the depth/height meter 3120 shown in FIG. 11A.

It can be appreciated that any suitable feedback component may be used in accordance with the present disclosure. As discussed, the feedback component may include a user interface, apparatus or other unit that receives a feedback signal and generates feedback to assist a rescuer/user in providing quality ACD CPR to a patient. Various forms of feedback are described herein, for example, visual feedback involving a display interface having textual and/or graphical feedback information, audio feedback from a speaker or other audio device to provide verbal, non-verbal, tonal and/or other audible feedback, haptic feedback which provides tactile indications of how the user may adjust the manner in which ACD CPR is administered, amongst others.

The portable defibrillator 312 is shown in a deployed state and is connected to the patient 302. In addition to providing defibrillation, the defibrillator 312 can serve as a patient monitor via a variety of sensors or sensor packages. For example, as shown here, electrodes 315 have been applied to the bare chest of the patient 302 and have been connected to the defibrillator 312, so that electrical shocking pulses can be provided to the electrodes in an effort to defibrillate the patient 302, and electrocardiogram (ECG) signals can be read from the patient 302. The defibrillator 312 can provide feedback in a conventional and known manner to an onsite rescuer, such as emergency medical personnel 306a and 306b.

In some implementations, additional therapeutic delivery devices (not shown) can be used to deliver the appropriate therapy to the patient. The therapeutic delivery devices can be, for example, a drug infusion device, an automatic ventilator and/or a device that includes multiple therapies such as defibrillation, chest compression, ventilation, and drug infusion. The therapeutic delivery devices are physically separate from the defibrillator 312, and control of the therapeutic delivery devices can be accomplished by a communications link from the defibrillator 312 that can be wired, wireless, or both.

In some implementations, control and coordination for the overall resuscitation treatment and the delivery of the various therapies can be accomplished through optimized chest compressions and decompressions, optionally based on rescuer's profile, by a processor that is integrated in the defibrillator 312 or is external to the defibrillator 312, such as the computing device 310 that is controlled by remote medical personnel 308. For instance, the computing device 310 can retrieve and process signals indicative of ACD CPR chest compression treatment (e.g., the force applied by the rescuer 306a through the ACD CPR chest compression system 304 and/or patient's chest wall displacement relative to time) and ECG data from the defibrillator 312.

The computing device 310 can analyze the signals to determine one or more parameters indicative of ACD CPR chest compression treatment. The parameters can include transition points, applied pressure, motion of the patient's chest wall (e.g., patient's chest wall velocity, displacement, and/or acceleration), compliance of patient's chest wall, adherence of the adhesive pad of the ACD CPR chest compression system 304, an angle of compression and decompression, and/or other parameters. Transition points define a transition between phases of the ACD CPR chest compression treatment, such as between a non-elevated phase and an elevated phase. The identification that a transition point has been reached can be determined from at least one of a displacement information and a force information.

Force measurements obtained from a force sensor may be processed by itself or in combination with other measurements to provide useful information in assisting the acute care provider in performing resuscitative treatment. For instance, the force measurement can be directly converted into pressure data, the surface of the force application being known. In addition, the measurement of patient's chest wall displacement relative to time can be converted into velocity measurement. The velocity can be used to determine how long the chest is held at a particular pressure. The area under the curve of the patient's chest wall velocity can be used as a key factor regarding optimized blood flow. The displacement measurement of the patient's chest wall and the force measurement can be used to determine the compliance of the patient's chest wall, expressed as the distance over force (e.g., cm/N) and represented in terms of an X/Y loop and/or as discrete number values. The adherence degree (or partial separation) of the adhesive pad can be determined by analyzing signals from an accelerometer attached to the adhesive pad and a second accelerometer attached to the handle. For example, a displacement of the adhesive pad recorded while the chest does not move, may indicate that the adhesive pad is detached from the patient's chest wall. The angle of compression and decompression can be determined to provide feedback to the user to push and pull in directions perpendicular to the chest. The angle of compression and decompression can be determined by using multiple force/acceleration sensors placed at various locations within the ACD CPR chest compression system 304. A 3-axis accelerometer may also be used to determine the angles of compression and decompression.

In parallel with analyzing the parameters indicative of ACD CPR chest compression treatment, the computing device 310 can process ECG signals, and perform relevant determinations to optimize the amplitude and the frequency of the force applied by the rescuer 306a and therefore optimize ACD CPR chest compression treatment delivery. In some implementations, the processor integrated in the defibrillator 312 or a processor integrated in the ACD CPR chest compression system 304 can perform all the processing of the force applied by the rescuer 306a of the rescuer 306a and the ECG, and can display a suitable level of feedback to the rescuers 306a and 306b. The defibrillator 312 can also transmit to a separate device (e.g., ACD CPR chest compression system 304) particular sets of processed data, and in response, the separate device can perform particular control actions.

An electrode assembly 315 is illustrated as being attached to the patient 302 in a standard position. The electrode assembly 315, in this example, is an assembly that combines an electrode positioned high on the right side of the patient's torso and an electrode positioned low on the left side of the patient's torso, along with a sensor package located over the patient's sternum (e.g. ZOLL Medical CPR Stat Padz®, Chelmsford MA). The sensor package, which is obscured in the figure by the hands of rescuer 306a in this example, can include an accelerometer or similar sensor package that can be used in cooperation with a computer in the defibrillator 312 to generate an overall quality score for the chest compressions and decompressions, and the quality score can indicate instantaneous quality or average quality across a time. For example, as a simplified description, signals from an accelerometer can be double integrated to identify a vertical displacement of the sensor package, and in turn of the sternum of the patient 302, to identify the magnitude of each chest compression and decompression. The time between receiving such input from the sensor package can be used to identify the pace at which chest compressions and decompressions are being applied to the patient 302.

The defibrillator 312 in this example is connected to the electrode package 315 and can operate according to standard protocol (e.g., to provide defibrillating shocks to the electrode package 315). The defibrillator can be a professional defibrillator, such as the R SERIES, M SERIES, E SERIES, or X SERIES from ZOLL Medical Corporation of Chelmsford, MA, or an automated external defibrillator (AED), including the AED PLUS, AED PRO, or ZOLL AED 3 from ZOLL Medical Corporation. The defibrillator is shown in one position relative to the rescuers 306a and 306b here, but can be placed in other locations to better present information to them, such as in the form of lights, displays, vibrators, or audible sound generators on a chest-mounted component such as an electrode or via an addressable earpiece for each of the rescuers. Such feedback, as discussed more fully below, can be on units that are separate from the main housing of the defibrillator, and that can communicate information about the patient 302 and performance of CPR chest compression to the defibrillator 312 or can receive feedback information from the defibrillator 312, through either wired or wireless connects that are made directly with the defibrillator 312 or indirectly through another device or devices.

In some implementations, the ACD CPR chest compression system 304 and the defibrillator 312 can be connected to the network 318 to transmit the acquired data to a computing device 310 that can be operated by the remote medical personnel 308. The CPR chest compression data transmitted by the ACD CPR chest compression system 304 and the defibrillator 312 to the computing device 310 can include data associated with the performance of the rescuer 306a and data associated with the response of the patient 302 to CPR chest compression. The ACD CPR chest compression system 304 can send information about the performance of chest compressions and decompressions, such as depth, rate, force, velocity, work, ventilation parameter(s), and/or other information for the chest compressions and decompressions. The defibrillator 312 can send ECG data and information related to characteristics of defibrillation signals. The computing device 310 can also receive data from the other sensors associated with the patient 302 such as an airflow sensor attached to or otherwise provided with a ventilation bag 307.

A central server system 320 can communicate with the computing device 310 or other devices at the rescue scene over a wireless network and/or a network 318, which can include portions of the Internet (where data can be appropriately encrypted to protect privacy). The central server system 320 can be provided as a server, or a virtual server, that runs server software components, and can include data storage including, but not limited to, a database and/or flat files. The central server system 320 can be part of a larger system of a healthcare continuum, in which patient data 322 and rescuer profiles 324, 326, and 328 are stored. Patient data 302 can be associated with an identification number or other identifier, and stored by the central server system 320 for later access.

Additionally, the central server system 320 can store patient profiles that include patient characteristics associated with the ACD CPR chest compression treatment and one or more parameters descriptive of the ACD CPR chest compression treatment. A patient profile can include age, gender, body-mass index, medical history (e.g., including known bone diseases that can affect rib cage compliance) and other patient characteristics relevant in selecting and optimizing the ACD CPR chest compression treatment. The parameters descriptive of the ACD CPR chest compression treatment can include parameters descriptive of the compression and decompression, such as force amplitude, impulse, distance, average force, peak force, etc., that can be calculated knowing the time of occurrence of the transition between the phases of the ACD CPR chest compression treatment.

Users interacting with the system 300 can access the data in the central server system 320. For example, as shown in FIG. 3, medical personnel 308, operating a computing device 310 that communicates wirelessly, such as over a cellular data network can access current and past CPR chest compression data. As such, the medical personnel 308 can review CPR chest compression data stored in the central server system 320. In this manner, the system 300 permits various portable electronic devices to communicate with each other so as to coordinate and optimize care that is provided to a patient 302 based on the patient profile treated at the rescue scene.

Example system 300 can provide real-time feedback to the rescuers 306a and 306b. For example, the defibrillator 312 or a display of a computing device can provide a prompt to guide the rescuers 306a and 306b in performing each phase of the ACD CPR chest compression treatment. The prompt can include at least one of an audio prompt, a verbal prompt, a non-verbal prompt, a visual prompt, a graphical prompt and a haptic prompt. Further details about the systems and methods of providing the prompt are described in detail with reference to FIG. 6. The process of observing the quality of a component of the CPR chest compression, such as the quality of each phase of ACD CPR chest compression treatment, can continue recursively as long as care is being provided to the patient 302. In some implementations, trends in the quality of a particular CPR chest compression component can be tracked so that the defibrillator 312 can distinguish situations, in which a rescuer is giving a poor chest compressions and decompressions because he or she was trying to find the appropriate rhythm or was distracted by a temporary problem, from situations in which the user truly is tiring and rescuer's position can be optimized.

In some instances, the defibrillator 312 and/or the ACD CPR chest compression system 304 can be adaptable to different CPR protocols. For example, the defibrillator 312 and/or the ACD CPR chest compression system 304 can be programmed according to a protocol that is personalized based on one or more parameters, such as patient characteristics, patient's medical conditions and patient's response to treatment. Some parameters can be automatically measured and processed by the ACD CPR chest compression system and some parameters can be entered by the rescuers. Protocols can be generally configured based on AHA guidelines. The protocols can include the duration of each phase of the ACD CPR chest compression treatment, one or more force parameters that can be applied during each of the phases (e.g., the force variation, force amplitude, force thresholds, and angles for applying the force). In some implementations, a rescuer, such as a medical director or an experienced rescuer, can alter such guidelines to fit particular patient needs, according to professional judgment.

In such a situation, the defibrillator 312 and/or the ACD CPR chest compression system 304 can be programmed with the parameters for each of the protocols, and an operator of the defibrillator 312 can select a protocol to be executed by the defibrillator 312 (or the protocol can have been selected by a medical director) and the protocol to be executed by the ACD CPR chest compression system 304. Such a selection can occur at the time of a rescue, or at a prior time. For example, the ability to select a protocol can be differentiated based on access privileges, such as a person who runs an EMT service (e.g., a medical director of appropriate training and certification to make such a determination). A user interacting with the defibrillator 312 and/or the ACD CPR chest compression system 304 can select the protocol to be followed on each of the machines operated by the service, and other users can be prevented from making particular changes, if lacking access privileges. In this manner, the defibrillator 312 and/or the ACD CPR chest compression system 304 can be caused to match its performance to whatever protocol its users have been trained to.

Using the techniques described here, the defibrillator 112 can, in addition to providing defibrillation shocks, ECG analysis, and other features traditionally provided by a defibrillator, also provide indications to optimize the data related to compression and decompression in real-time and/or to switch rescuers between various components of providing CPR and other care to a patient. The defibrillator can be deployed in the same manner as existing defibrillators, but can provide additional functionality in a manner that can be easily understood by trained and untrained rescuers.

Figure 4A:
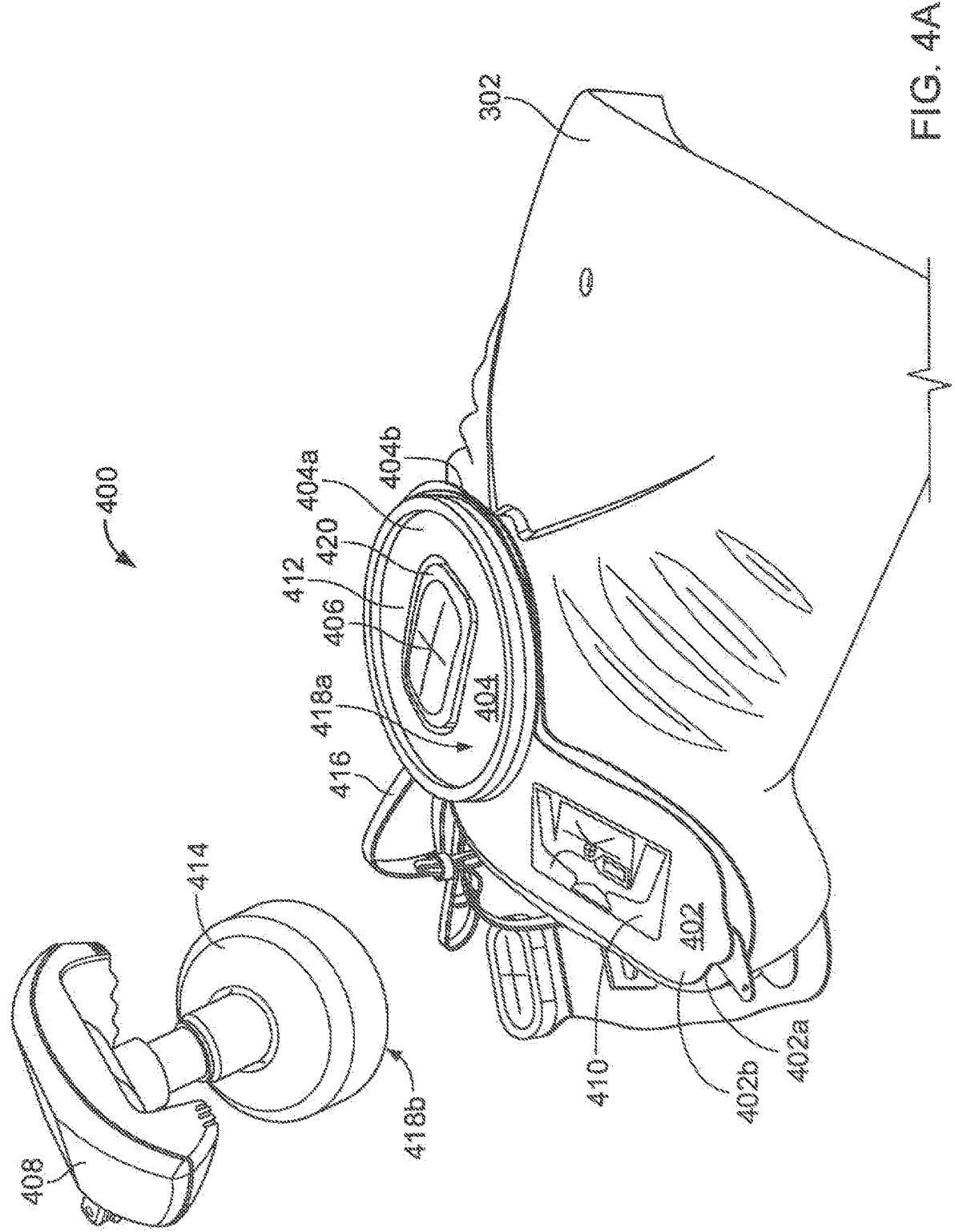
FIGS. 4A and 4B show frontal and perspective views of the CPR chest compression assistance system in accordance with an embodiment.
Figure 4B:
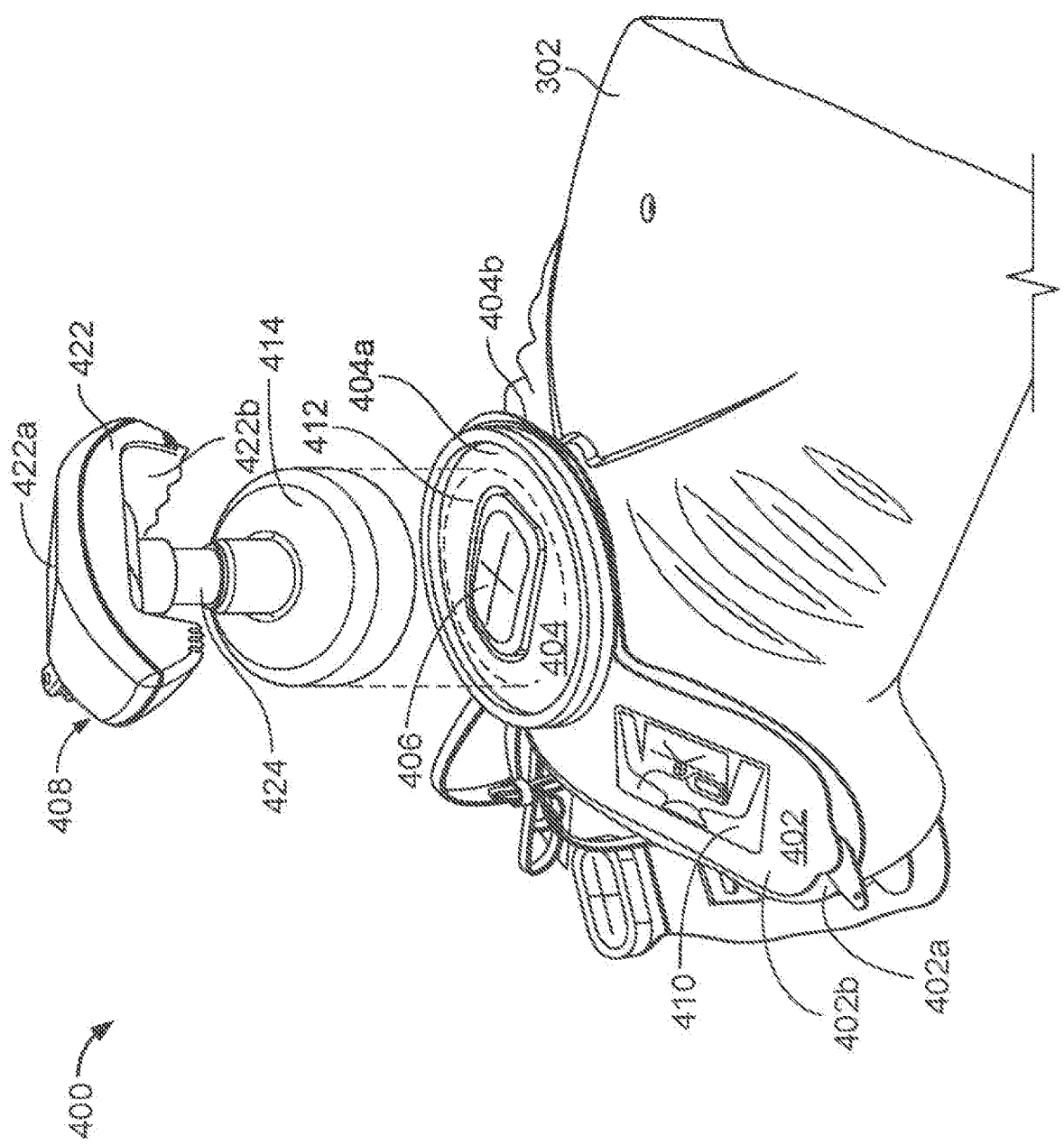

FIGS. 4A and 4B illustrate examples of components of an ACD CPR chest compression system 400 (e.g., ACD CPR chest compression system 304 described with reference to FIG. 3) that can be used to deliver a CPR chest compression treatment to the patient 302. The example components of the ACD CPR chest compression system 400 can include an adhesive pad 402, a coupling surface 404, a sensor 406, and an ACD device 408.

The adhesive pad 402 can include an alignment feature 410. The alignment feature 410 can be included in the upward facing portion of the adhesive pad 402. The alignment feature 410 can guide a rescuer in attaching the adhesive pad 402 to an optimal portion of the patient's chest. The adhesive pad 402 can include a liner 402a and an adhesive face 402b. The liner 402a can be removed or peeled away from adhesive face 402b by a rescuer to attach the adhesive pad 402 to the patient 302. The adhesive face 402b can be configured to be releasably attached to the patient's chest, for example on the sternum at the mid-nipple line as shown in FIGS. 4A-4D.

The adhesive face 402b can include a layer of high-traction or anti-slip material for contacting the skin of the patient 302, such that the adhesive pad 402 remains attached to the patient's skin during CPR chest compression treatment. In some implementations, the adhesive face 402b can include pressure-sensitive adhesives, such as medical bandage adhesives, transdermal patches, and other medical applications. In some implementations, the adhesive face 402b can include natural and synthetic rubber-based formulations, such as polyisobutylenes, and acrylic and silicon-based materials, and swollen hydrogels, such as polyvinyl pyrrolidone, which are suitable in conjunction with electrodes. At completion of a CPR chest compression treatment with the ACD CPR chest compression system 400, the adhesive face 402b can be removed from the patient's chest.

The dimensions of adhesive pad 402 can be chosen to provide a desired contact area with the patient's chest. In some implementations, the larger the surface of the adhesive pad 402, the more expansion of chest can be achieved using ACD CPR chest compression system 400 (e.g., if the patient's chest is compliant or if a rib has been broken). Typically, for adult patients, adhesive pad 402 can have a generally square or rectangular shape. For children, the dimensions can be smaller. Other shapes can also be useful. For example, it can be desirable to shape the lower surface 402a of the adhesive pad 402 to conform to the general contours of the patient's chest. In addition, it may be desirable to provide a plurality of sizes and shapes of adhesive pads 402 in a single kit so that an adhesive pad 402 can be selected for the individual patient 302. The thickness of the adhesive pad 402 can depend on the resiliency of the material employed. For manual CPR chest compression operation, the adhesive pad 402 can be about 30 cm by 40 cm.

The adhesive pad 402 can include an electrode configured to transmit a defibrillation current to the patient 302. The adhesive pad 402 can include or be coupled to the sensor 406. The sensor 406 can be configured to measure at least one chest compression parameter during CPR chest compression treatment. A wire 416 can provide an electrical connection between the sensor 406 and a medical device (e.g., the defibrillator 312 described with reference to FIG. 3). For example, the sensor 406 can be used to assess and display the condition of the patient 302 prior to and during the CPR chest compression treatment. In some cases, the signals detected by the sensor 406 are used to initiate and optimize the CPR chest compression treatment. Examples of electrode and sensor configurations are further described with reference to FIG. 6

In some implementations, the coupling surface 404 at least partially surrounds the sensor 406 and/or at least a portion of the wire 416. The coupling surface 404 can be an integrated part of the adhesive pad 402 or it can be releasably attached to the adhesive pad 402. The coupling surface 402 includes an upward facing portion 404a and a downward facing portion 404b. The downward facing portion 404b can be configured to maintain adherence with the adhesive pad 402. The upward facing portion 404a can be configured to maintain adherence with the ACD device 408. The adherence between the coupling surface 404 and the ACD device 408 can be sufficient to transfer a decompression force between the ACD device 408 and the patient's chest during the CPR chest compression treatment without detaching. The upward facing portion 404a can be substantially smooth.

The ACD device 408 can include an applicator body 414, a handle 422, and a stem 424. The applicator body 414 can be made of a deformable rubberized material, and it comprises a body portion and a seal portion, which extends integrally from one end of the body portion. The applicator body 414 is formed in a substantially circular, rounded, open, cup-shaped configuration so that it has an enlarged open end and a reduced end that is attached to the handle 422. An enlarged open interior area or cavity is formed in the applicator body 414 so that it opens outwardly through the open end. The applicator body 414 is further described in detail with reference to FIGS. 5C-5E.

Figure 4C:
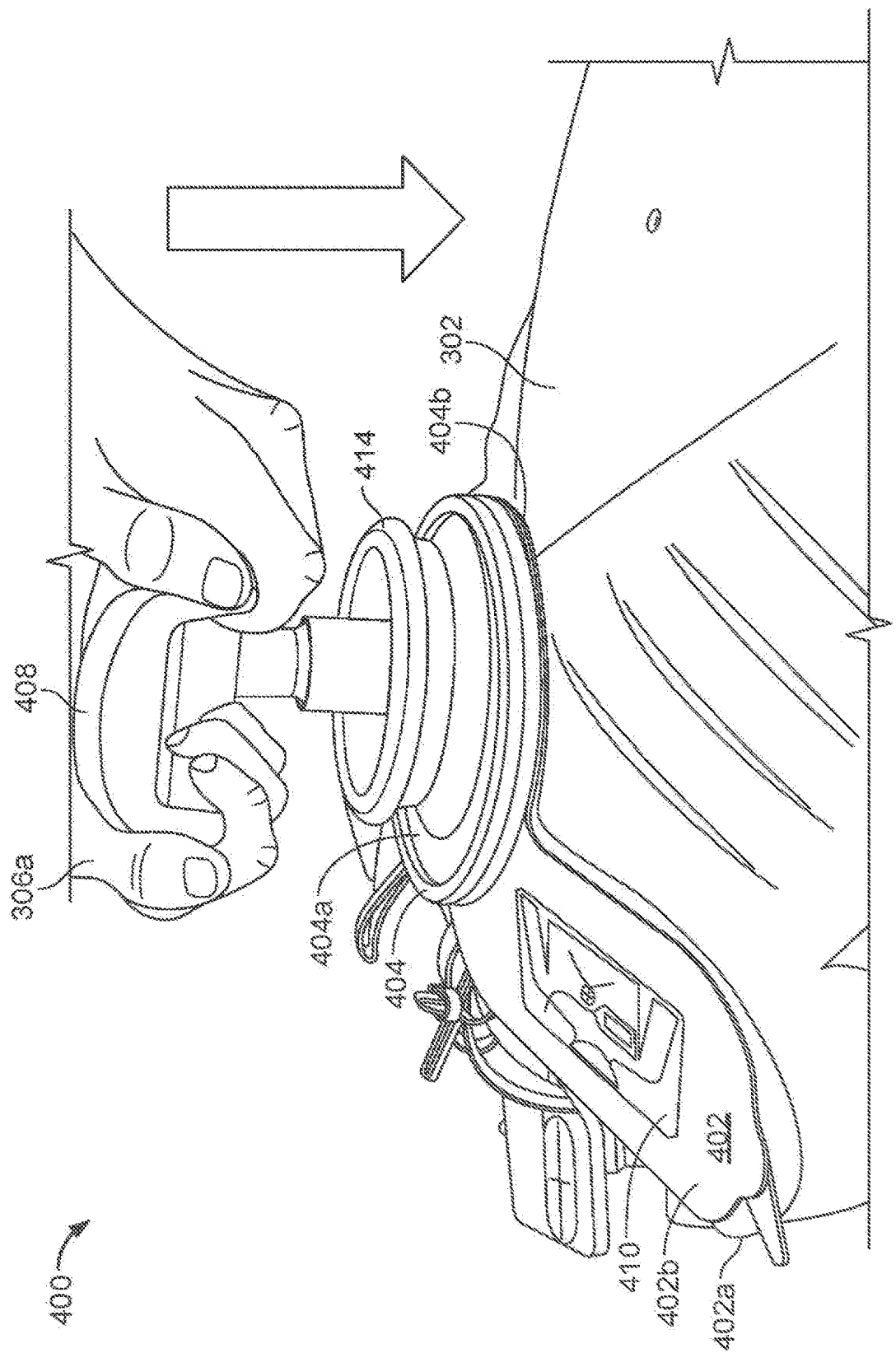
FIGS. 4C and 4D show perspective views the CPR chest compression assistance system according to compression and active decompression protocols.
Figure 4D:
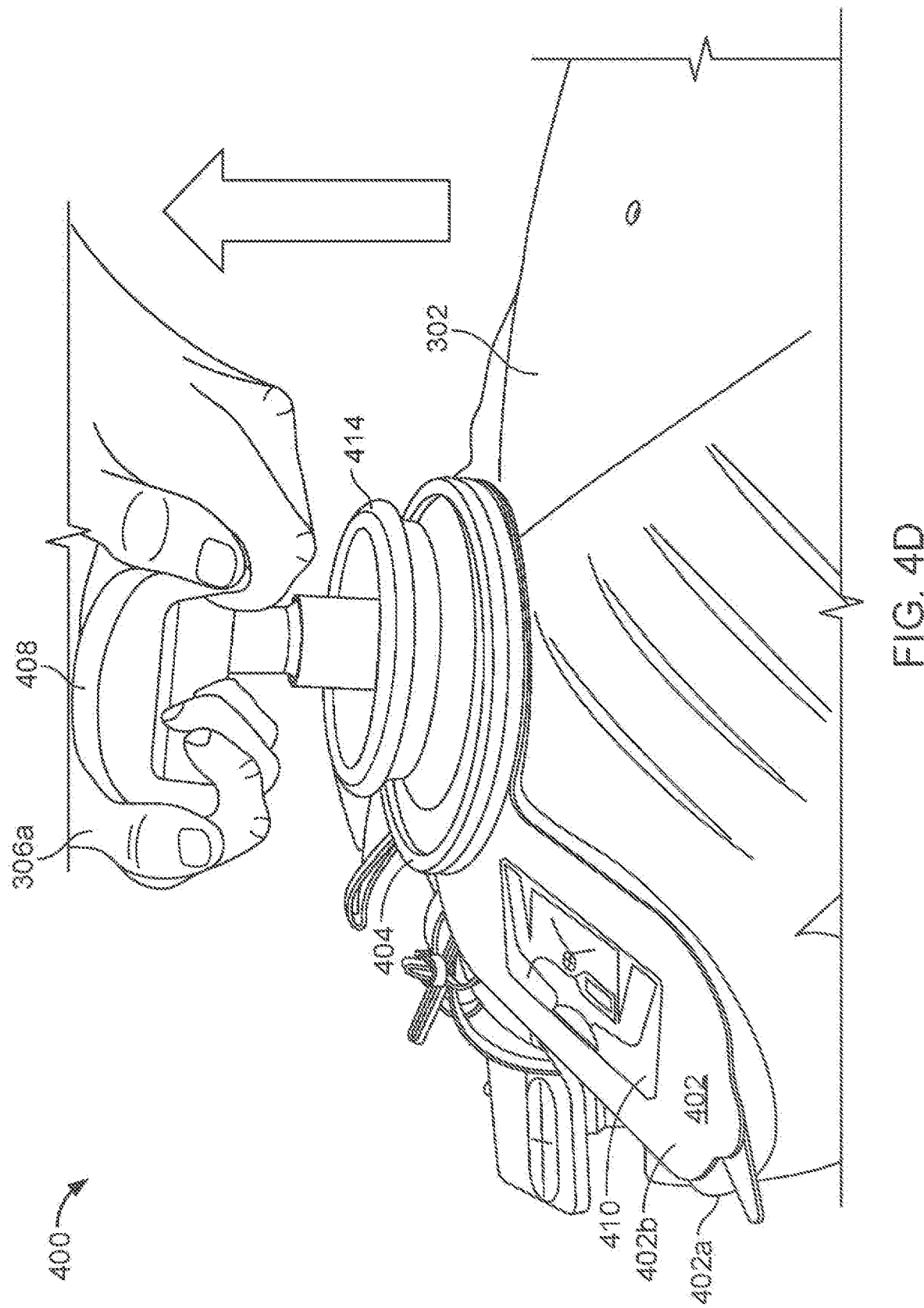

The handle 422 includes a dome-shaped upper surface 422a and an annular planar lower surface 422b separated by a peripheral flange. The top of stem 424 is centrally located within annular lower surface 422b of the handle 422 and the bottom of stem 424 is centrally located on the upper surface 404a of the coupling surface 404. The cross-section of the applicator body 414 defines the dimensions of compressive/decompressive area, such as landing pad 412. The handle 422 is shaped to enable rescuer's hands to optimally grasp the handle 422 with the palms resting on the upper surface 422a, the fingers wrapped around ridge of the handle and the finger tips positioned against lower surface 422b (FIGS. 4C and 4D). Handle 422 and connective stem 424 can be constructed from a suitable rigid material, e.g. a molded plastic. Handle 422 can be filled with a gel, foam, padding or the like to enhance its shock-absorbing and distributing capability.

The coupling surface 404 can include a landing pad 412 for the applicator body 414 of the ACD device 408. The landing pad 412 includes a surface that complements, for example, as size and geometry, the applicator body 414. In some implementations, the coupling surface 404 includes a compliant and resilient material, such as a natural or synthetic foam. In some implementations, the coupling surface 404 includes an attachment member 418a complementary to a corresponding attachment member 418b of the ACD device 408. Each of the mechanical attachment members 418a and 418b can include a mating interface. The attachment members 418a and 418b can include mechanical gearing, hydraulics, pneumatics, and/or electromagnetic coupling. For example, the attachment members 418a and 418b can form a pneumatic system for increasing or enhancing a vacuum between the applicator body 414 and the coupling surface 404. The attachment members 418a and 418b can also be configured to act as actuators to release the vacuum holds of the attached applicator body 414 from the coupling surface 404, for instance, by injecting air into the applicator body 414. The attachment members 418a and 418b can include well-known components such as a pump, valves, and/or fluid transfer lines.

In some implementations, the ACD CPR chest compression system 400 includes a passageway 420 located between the sensor 406 and the coupling surface 404. The passageway 420 can be configured to optimize the propagation of the compression and decompression forces from the ACD device 408 to the patient's chest. The dimensions of passageway 420 can be chosen to relative to the base of the applicator body 418 and the surface of the sensor 406. For example, the passageway 420 can substantially encircle the sensor 406, such that the inner diameter of the passageway 420 is at least equal or larger than the outer diameter of the sensor 406. The passageway 420 can be completely encircled by the base of the applicator body 418, such that the outer diameter of the passageway 420 is at least equal or smaller than the inner diameter of the base of the applicator body 418. The passageway 420 can have multiple configurations and structures.

FIGS. 4C and 4D illustrate a perspective view of the ACD CPR chest compression system 400, in which the ACD device 408 is attached to the coupling surface 404. The illustrated arrangement of the ACD CPR chest compression system 400 can be used by a rescuer (e.g., 306a described with reference to FIG. 3) for performing both active compressions (FIG. 4C) and decompressions (FIG. 4D) for manual CPR chest compression treatment. The configuration of the ACD device 408 enables the rescuer 306 to press down on upper surface 422a of handle 422 with the palms of the hands to apply a compressive force against coupling surface 404 and patient's chest over a compressive/decompressive area, such as landing pad 412. The configuration of the ACD device 408 also allows the operator to lift up by pressing on the lower surface 422b of the handle 422 with the fingers. Since lower surface 402a of adhesive pad 402 is adhered to contact area of patient's chest, the lifting motion on handle 422 lifts and expands patient's chest.

FIG. 5A illustrates a top view of an ACD device 500 (e.g., ACD device 208 in FIG. 4A). The ACD device 500 includes a handle 510 and an applicator body 530. The handle 510 has two handgrips 510a, 510b and a local feedback display 537. The ACD device 500 can be configured for being used to assist with multiple CPR chest compression treatments. The ACD device 500 can be switched on and turned off by pressing and holding down the power button 502 for a predetermined amount of time, for example 5 seconds. During this time, the local feedback display 537 can display the remaining battery life in time units (e.g., hours). If the power button is not held for a sufficient amount of time (e.g. 5 seconds) the ACD device 500 can remain on, and it automatically power off after 5 minutes if no compressions are sensed.

The ACD device 500 can be configured to provide a predetermined number of hours of use. For example, the ACD device 500 can be designed to provide about 30 hours of use. At any time, a rescuer can determine the remaining battery life by pressing and holding a power button. The local feedback display 537 can display the amount of time remaining, for example by displaying the letter H followed by a number. The number can indicate the number of hours of battery life remaining. In some implementations, the local feedback display 537 can display an alert when the ACD device 500 has less than one hour of battery life remaining.

The handle 510 is attached to the applicator body 530. The applicator body 530 can be releasably attached to a coupling surface 522 (e.g., coupling surface 404 described with reference to FIG. 4A) that is attached via a contact adhesive 523 to the patient's skin 520. In some implementations, the applicator body 530 can be attached to the coupling surface 522 via a magnet. In some implementations, the magnetic coupling is configured such that applicator body 530 becomes detached from coupling surface 522 when excessive decompression force (upward pull) is applied. Other means to couple the applicator body 530 to the coupling surface 522 include various mechanical connections including ball and socket, cantilevered arm, or detent mechanism or the like.

Figure 11A:
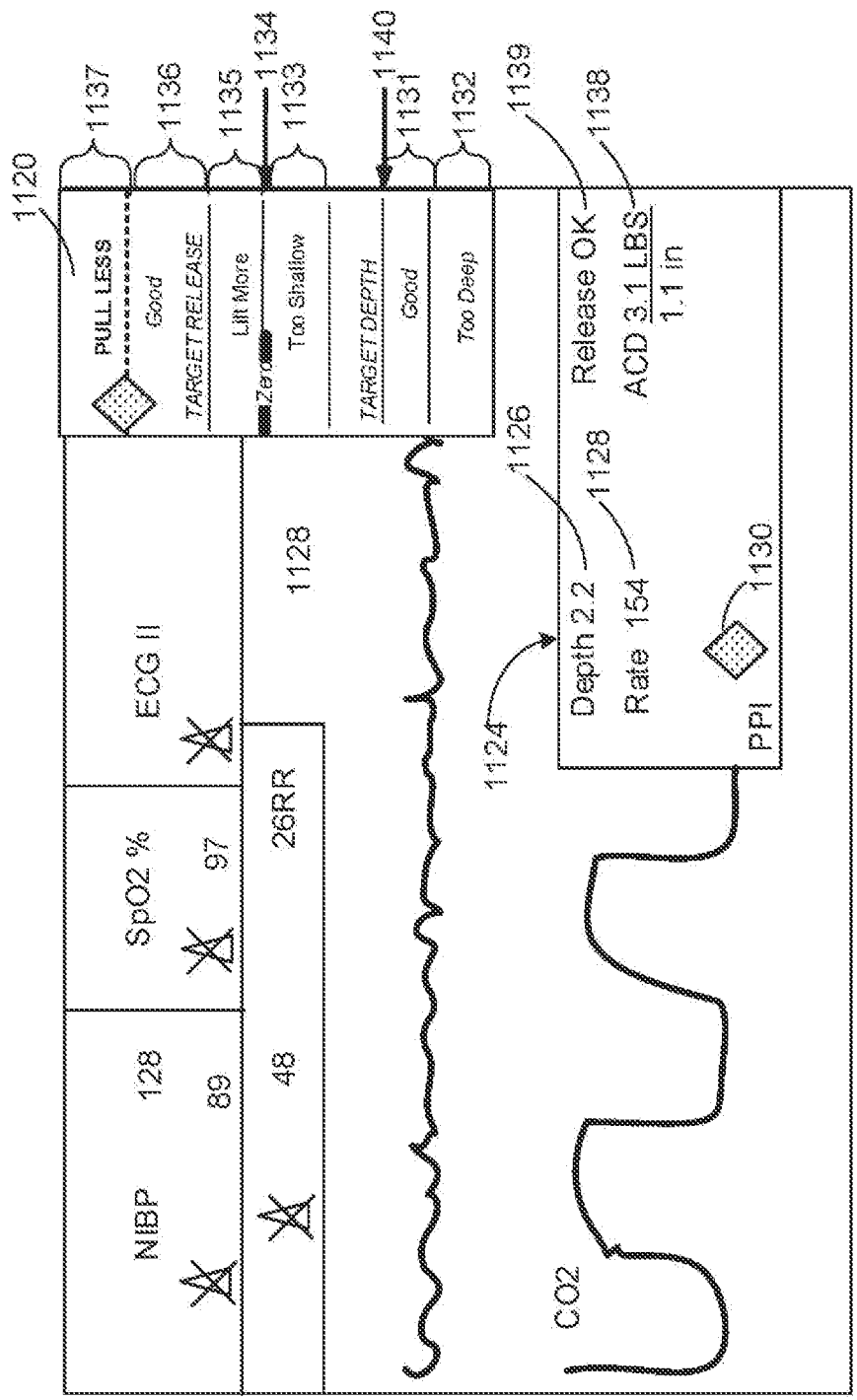
FIGS. 11A and 11B show screenshots of a display providing ACD CPR feedback.

FIG. 5B illustrates an example of a magnetic coupling mechanism in an external chest compression and decompression system. FIG. 5B provides a cross-section view of compression and decompression the ACD device 500, which includes an applicator body 530 releasably coupled to the coupling surface 522, which is attached to an adhesive pad 522 that is attached to the patient's skin 520. The ACD device 500 can include a plurality of sensors 532, 533, 534 and 539, a processor circuit 535 containing, e.g., the sensor signal acquisition, microprocessor, power supply, communications, etc., other electronics, a battery 536, a local feedback display 537, a coupling mechanism 550 between the coupling surface 522 and the applicator body 512. Sensor 532 can be a decompression force sensor. Sensor 533 can be a compression force sensor. Sensor 534 can be an accelerometer or other type of motion sensor. Sensor 539 can be a tilt and off axis motion sensor. Each of the plurality of sensors 532, 533, 534 and 539 can generate signals to monitor and optimize ACD CPR chest compression treatment (e.g., by assisting with identification of different treatment phases and transition points, as described with reference to FIG. 1). The measurements of the signals detected by the sensors 532, 533, 534 and 539 can be displayed on the local feedback display 537, as illustrated in FIG. 11A.

The coupling mechanism 560 can include a magnet 540 and a magnet keeper 550. In some implementations, the magnet 540 can include or be part of a magnet assembly having a magnet, a non-ferrous spacer, and a ferrous container for directing the magnetic flux from the pole of the magnet furthest away from the magnet keeper to the magnet keeper. The poles of the magnet can be arranged such that the poles are aligned along the axis 580 of the system piston 570. The magnetic keeper 550 on the coupling surface 522 of the ACD device 500 can include a magnet with poles arranged in the opposite direction of the system handle magnet or of a ferrous material such as 12L14 carbon steel having a high capacity for carrying magnetic flux. A magnetic coupling between the applicator body 530 and the coupling surface 522 can be effortless. In some implementations, the force of the disconnection of the magnetic coupling can be stable over a wide range of operating environments.

In some implementations, a magnetic coupler mechanism 518 can include a magnet assembly disposed on or coupled with the applicator body 530, and a keeper assembly disposed on or coupled with the coupling surface 522. For example, a magnetic coupler mechanism 518 can include magnet 540, or magnet assembly, and keeper assembly 550. The magnet 540 or magnet assembly can be coupled with (or part of) the applicator body 530. The keeper assembly 550 can be coupled with or part of the coupling surface 522. The magnet assembly and keeper assembly 550 in combination can be referred to as a coupler assembly. In some implementations, the coupler assembly can operate to provide a consistent release force allowing the applicator body 530 to separate from the coupling surface 522 prior to the adhesive pad releasing from the patient' skin 520. In addition, it may be desirable that the magnet assembly does not have a magnetic field that is widely dispersed, but approximately focused in the direction of the keeper. To focus the magnetic field, the magnet assembly can include a magnetic core, a non-magnetic sleeve, and a ferromagnetic pot which conducts the magnetic flux from the pole on the enclosed side of the magnet to the open side of the magnet. The arrangement of a jacket with the magnet can focus the majority of the magnetic flux to the open end of the assembly. For example, the magnet assembly may include a magnetic ore 540, a non-magnetic sleeve, and a ferromagnetic pot, which conducts the magnetic flux from the pole on the enclosed side 540 of the magnet to the open side 540 of the magnet. The arrangement of a jacket with the magnet can focus the majority of the magnetic flux to the open end of the assembly. Control or selection of the material properties of the keeper 550 can be helpful to achieve a consistent release force. In some implementations, the material can have a high magnetic saturation such as a 12L14 or American Iron and Steel Institute (AISI) 1010 or 1020 material and the magnetic properties of the material can be controlled through the control of material temper. For example, materials can be processed to a fully annealed condition. In addition to the magnetic coupling mechanism described herein, other types of breakaway mechanisms can be used in an external chest compression and decompression for coupling the coupling surface 522 with the ACD device 500. Examples of breakaway mechanisms can be configured to allow the ACD device 500 to disengage from the coupling surface 522 in a controlled manner.

Figure 5D:
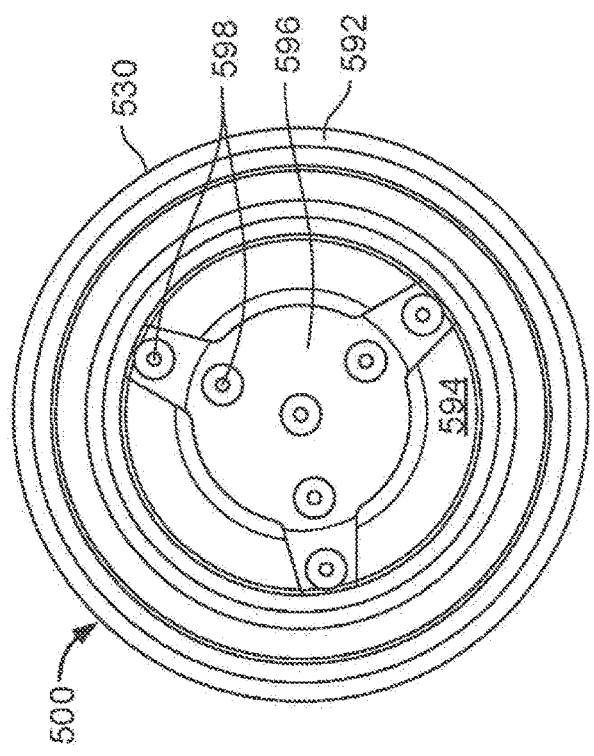
FIGS. 5C, 5D, and 5E show bottom views of an example ACD device in accordance with illustrative embodiments.
Figure 5C:
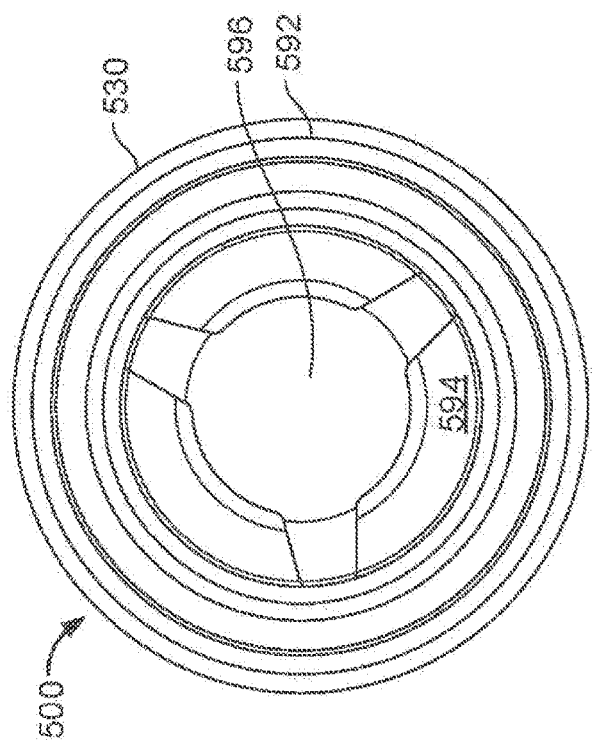
Figure 5E:
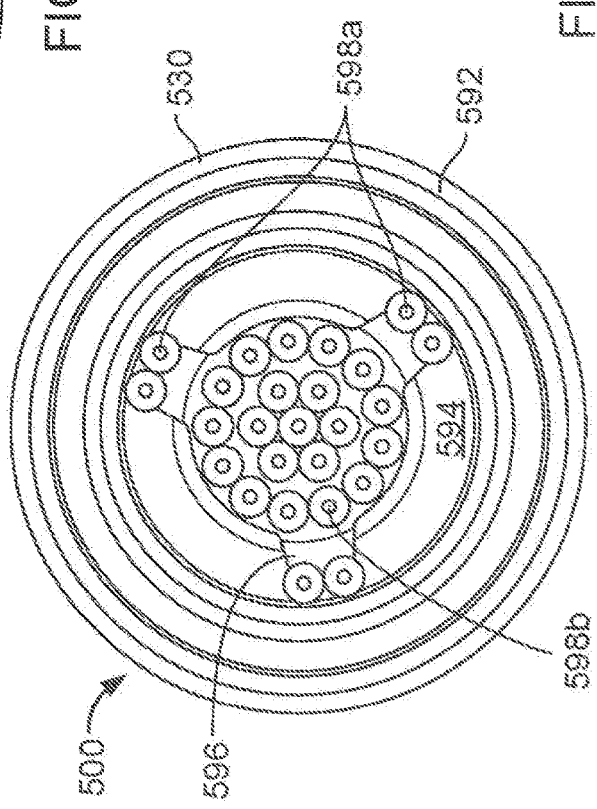

FIGS. 5C-5E illustrate examples of bottom views of the ACD device 500. The bottom views include the applicator body 530 of the ACD device 500 (e.g., applicator body 214 of the ACD device 208 described with reference to FIG. 2). In some implementations, the applicator body 530 can be a plunger. The applicator body 530 includes a distal end 592 and a proximal end 594. The proximal end 594 defines the part of the applicator body 530 that extends from the applicator body 530. The distal end 592 defines the part of the applicator body 530 that impacts the patient's chest through the coupling surface 522. The applicator body 530 can include one or more check valves allowing fluid to escape the passageway during attachment to the coupling surface 522, but preventing fluid from entering the passageway via the check valves. The check valves include one or more of duckbill valves, umbrella valves, cross slit valves, ball-check valves, cone-check valves, and swing valves.

In some implementations, the applicator body 530 includes a compression pad 596. The compression pad 596 can be a flexible surface element configured to regulate the force applied to the patient's chest through the air passageway of the coupling surface. The compression pad 596 can include an adhesive layer. The compression pad 596 can include one or more suction cups 598 that apply compression and decompression forces to patient's chest through the coupling surface 522. The adhesive layer can line the margins of the suction cups 598. The compression pad 596 can be secured to the coupling surface 522 by suction created by the suction cups 598 formed on distal end 592. A rescuer can pull back the ACD device 500, which in response extends the applicator body 530, to confirm secure coupling between the compression pad 596 and the coupling surface 522.

The compression pad 596 has a stiffness that increases from margins towards a geometrical center of the compression pad 596. The compression pad 596 can present any suitable complex shape, including multiple appendages, arms or lobes. Each arm or lobe of the compression pad 596 can contain numerous suction cups 598. The use of multiple lobes enables the compression pad 596 with many suction cups 598 to conform to irregularities in the top layer of the coupling surface 522 (e.g., irregularities due to sensor and wire inclusions). The lobes of the compression pad can be conformable and inelastic to convey the decompression force between ACD device 500 and the coupling surface 522.

In some implementations, the size and/or shape of the suction cups 598 can be selected based on one or more characteristics of the coupling surface 522. In some implementations, the number and the location of the suction cups 598 can be selected based on one or more characteristics of the coupling surface 522. For example, the suction cups 598 can be arranged in two groups 598a and 598b, distanced from each other, such that no suction cup covers the passageway of the coupling surface 522 during coupling between the compression pad 596 and the coupling surface 522.

Figure 6:
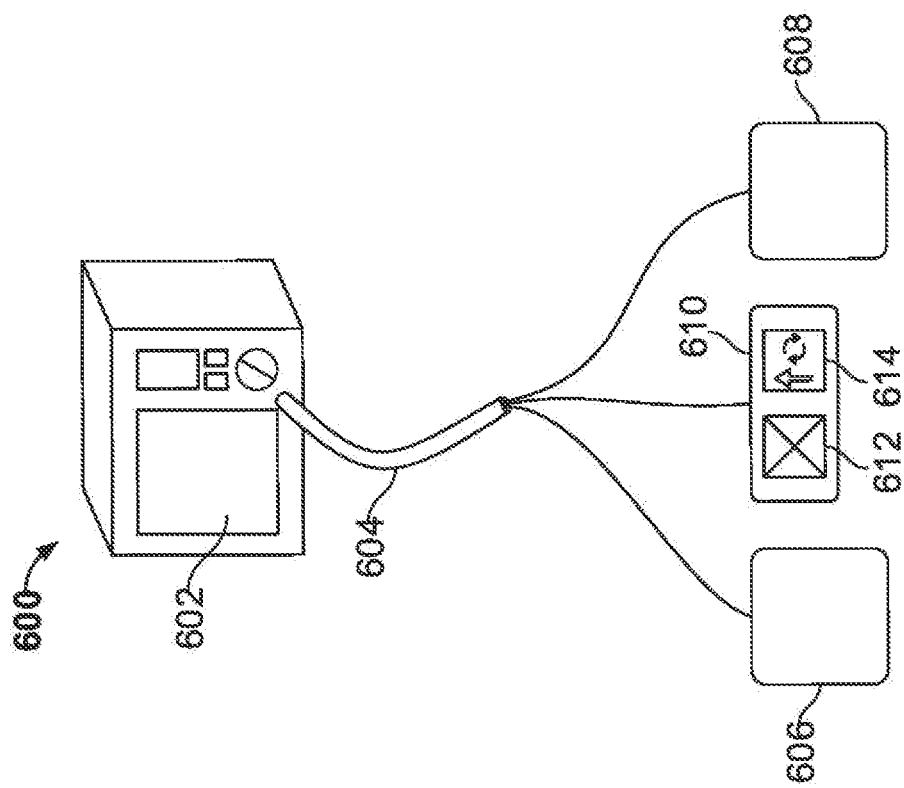
FIG. 6 shows a portable defibrillator and ancillary components arranged to provide feedback and instruction to rescuers in accordance with certain embodiments.

Referring to FIG. 6, an example system 600 is shown in which a defibrillator 602, including a standard configuration, is upgraded to provide an additional user feedback functionality. The defibrillator 602 is connected to an electrode assembly by way of a wiring harness 604. The wiring harness 604 can include a number of wire leads that are connected together by a common plastic shroud that can surround the wires or can have been integrally formed around the wires such as through an extrusion process, and can be connected to the defibrillator 602 by way of a single plug. For example, the defibrillator 602 can be provided with a female or male connection, and the plug can be provided with a corresponding connection in a manner that is well known in the art. The wires can carry power from the defibrillator 602, such as current to provide a shock to a patient who is being provided with emergency care, or to the defibrillator 602, such as in the form of signals for generating ECG information, accelerometer information, and measurements of trans-thoracic impedance of a patient.

The electrode assembly in this example includes a first electrode 606, a second electrode 608, and a chest compression assembly 610. The first electrode 606 can be configured to be placed above the patient's right breast, while the second electrode 608 can be configured to be placed below the patient's left breast. During a rescue operation, printed insignia on one or both of the electrodes 606, 608 can indicate to a rescuer how to deploy the electrodes 606, 608, and where each of them can be placed. In addition, the defibrillator 602 can display such instructions on a graphical display and can also provide verbal instructions to supplement was is shown in the visual instructions, such as instructions for the sequential operation of the defibrillator.

The chest compression assembly 610, in this example, includes a detector 612 and a display 614. The detector 612 can include a plastic housing within which is mounted an accelerator assembly. The accelerator assembly can move with the housing as chest compressions and decompressions are performed on a patient so that motion of the accelerometer matches motion of the patient's sternum. The detector 612 is shown in the figure as having an "X" printed on its top surface to indicate to the rescuer where to place his or her hands when delivering chest compressions and decompressions to a patient. The accelerator in the housing can be connected to pass signals through harness 604 to defibrillator 602 (or can include a wireless transceiver for passing the information wirelessly), which can be provided with circuitry and or software for converting such signals into the indications about the rate and depth of compressions and decompressions being performed on the patient, in manners such as those described below.

The display 614 can provide feedback that is directed to the rescuer who is performing chest compressions and decompressions. In this example, the feedback comprises symbols similar to those shown on the display of defibrillator 112 in FIG. 1, in particular, a real-time representation of the rescuer who performs chest compressions and decompressions synchronously displayed with an optimized rescuer position. The representation can be selected to be independent of the orientation from which it is viewed, so that it has the same meaning to a rescuer who is on the right side of the patient as to a rescuer who is on the left side of the patient. In that manner, the system 600 does not need to determine where the rescuer is positioned. Also, a haptic vibrating mechanism can be provided at the assembly 610, so as to provide tactile beats or metronomes for a user to follow in providing chest compressions and decompressions.

Figure 7:
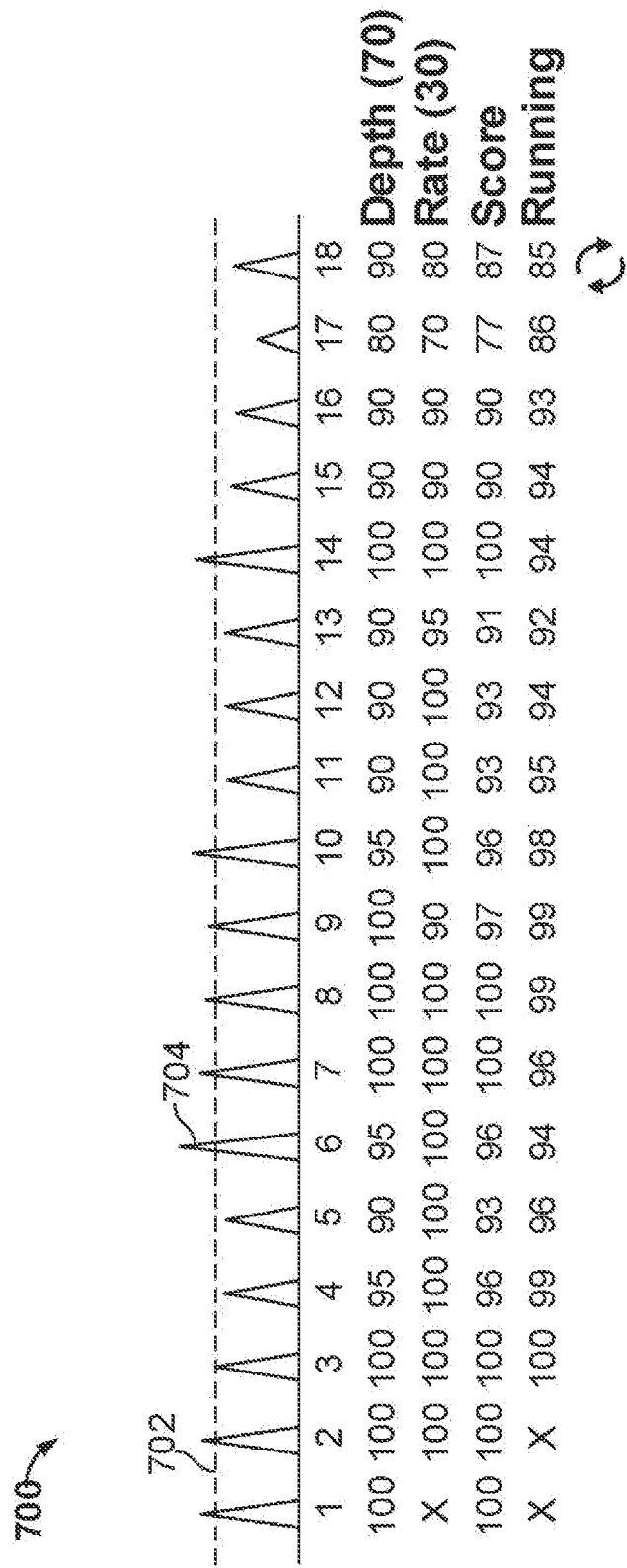
FIG. 7 shows example chest compression inputs and mechanisms for analyzing the inputs to determine whether a different person can provide chest compressions.

FIG. 7 shows example chest compression inputs and mechanisms for analyzing the inputs to determine whether a different rescuer can provide chest compressions and decompressions. In general, the illustrated example includes a series of eighteen chest compressions and decompressions 700 that have been graphed along a horizontal time axis, along with a variety of numbers that represent parameters of how the chest compressions and decompressions were performed. Such sensed compression data and derived numbers can then be used to determine when the quality of the chest compressions and decompressions indicates that the rescuer is getting fatigued and cannot maintain the optimized CPR chest compression technique identified by the system, and the system can indicate to the rescuer that they can switch with another, fresher rescuer.

Referring more specifically to the graphed compressions and decompressions, a dashed line 702 represents a target chest compression depth. Each of the spikes 704 indicate a distance level of downward compression (y axis), graphed according to time (x axis). In particular, the compressions and decompressions are sharp motions followed by pauses, with the overall pattern repeated eighteen times during the time (which can be a fraction of a minute when the rescuer is performing about 100 compressions and decompressions per minute). Such compressions and decompressions can be sensed by an accelerometer assembly that is between the hands of the rescuer performing chest compressions and decompressions and the sternum of the patient. Sensed signals can then be passed through a wiring harness to circuitry and software in a defibrillator or other medical device that can analyze the signals to identified compression depths and timing of the chest compressions and decompressions.

As can be seen, the initial chest compressions and decompressions are at an appropriate level and an appropriate rate, but began to dip at the fourth and fifth compressions and decompressions. The compressions and decompressions then pick up and hit the dashed line 702, perhaps because the fall in compressions and decompressions caused a defibrillator to indicate to a rescuer that they can compress harder, and the user followed such direction. The depth of compressions and decompressions over time then falls again at compressions and decompressions 11, 12 and 13, but then picks up at 14 and falls yet again near the end, indicating that the user has become fatigued.

Below the graph are shown numbers that, for this example, indicate values that can be computed by a defibrillator that is connected to a system for determining when to signal that a provider of chest compressions and decompressions to a patient can be changed by the system. The top row shows a score that can be given to a user to rate the quality of the depth of the chest compressions and decompressions. Such a score can be given a baseline of 100 around a depth that approximates the desired line of 702. The score can decrease proportional with the distance from line 702. The score can decrease faster for deviations on the under-compression side than for deviations on the over-compression side, e.g., if a determination is made that under-compression is a more serious error than over-compression. Thus, for example, the fifth compression falls below line 702 by an amount less than the sixth compression falls above the line, but the fifth compression receives a lower score than does the sixth compression.

In this example, the depth of compression factor is provided 70% of a weighting in determining an overall score for the quality of the chest compression. The other 70% of the score is driven by the rate at which the user provides the compressions and decompressions. For example, the feedback can display even spacing for compressions two through eight, but a slight delay for compression nine, so that the ninth compression receives a score of 90 instead of a score of 100. In addition, one can see lengthening delays between compressions and decompressions at the end of the period. The rate scores reflect, in each instance, how far a compression was performed from the time at which it was supposed to be performed according to protocol. Again, the scores are scaled to a maximum of 100 for ease of explanation, but could take other forms also.

The third line in the numbers indicates an overall score for each of the compressions and decompressions, where the overall score is simply the combined weighted value of the two component scores for depth and rate, respectively. Finally, the fourth line shows a running score that is a running average of the current score and the two previous scores. By using a running average, singular deviations from a perfect compression can be ignored, while lingering deviations can be captured so that continual failure by a user, which indicates fatigue of the user, can result in the generation of a signal to switch users in performing chest compressions and decompressions. Thus, for example, compression number five is a bad compression, but the running score is relatively high because the previous two compressions and decompressions were better.

In this example, the trigger for generating an indication that users can change position is a running score at or below 85. Thus, although the running score in the example rises and falls as a user has periodic problems with performing compressions and decompressions, it does not fall to the triggering level until compression eighteen, after there had been three weak compressions and decompressions in a row that were also spaced too far apart—so that the running average score really fell. In actual implementation, software can monitor the value as a user provides compressions and decompressions, can periodically update the value (e.g., once for each compression or on another basis), and can cause a defibrillator, such as defibrillator 112, to emit output to one or more rescuers to indicate the need for a change, such as the indication shown in the prior figures above.

While the particular running average scoring technique described is provided for its simplicity and ease of understanding, different approaches can be used to identify when a user is likely becoming too fatigued to maintain quality chest compressions and decompressions or other components of CPR chest compression. For example, various inputs can be subjected to derivations in order to determine rates of change of those inputs. An indication to change rescuers can be generated when the rate of change in the quality of performance exceeds a preset amount in a negative direction. Also, models can be generated to represent fatigued users, and actual inputs can be compared to such models to indicate when fatigue is setting in for a real user and to cause an alert to be generated.

In some instances, such as when the number of rescuers is known, data can be stored across multiple cycles of chest compression sessions for each of the users. For example, the system can identify in early cycles of a rescue that one of the rescuers has a sudden drop-off in chest compression performance but then recovers, and can store such understanding and use it in subsequent cycles so as to not trigger an indication to change rescuers simply because the particular rescuer is having momentary problems. Another rescuer can be seen to have a slower drop in performance but can be more erratic in his provision of chest compressions and decompressions, so that a system can permit more variability before it triggers an indication to switch rescuers, since variability by that user can not indicate fatigue, but can simply be standard variability in the manner in which the user performs chest compressions and decompressions. Other factors can also be taken into account in addition to depth and rate of providing chest compressions and decompressions. For example, a heart rate monitor can be applied to a rescuer and an increase in heart rate can indicate fatigue by the rescuer, and can be used to generate a signal to switch rescuers. Also, the shape of a compression profile can be used, such that a jerky or sharp profile can indicate fatigue by a user, and also contribute to the triggering of a signal to switch rescuers.

Figure 8:
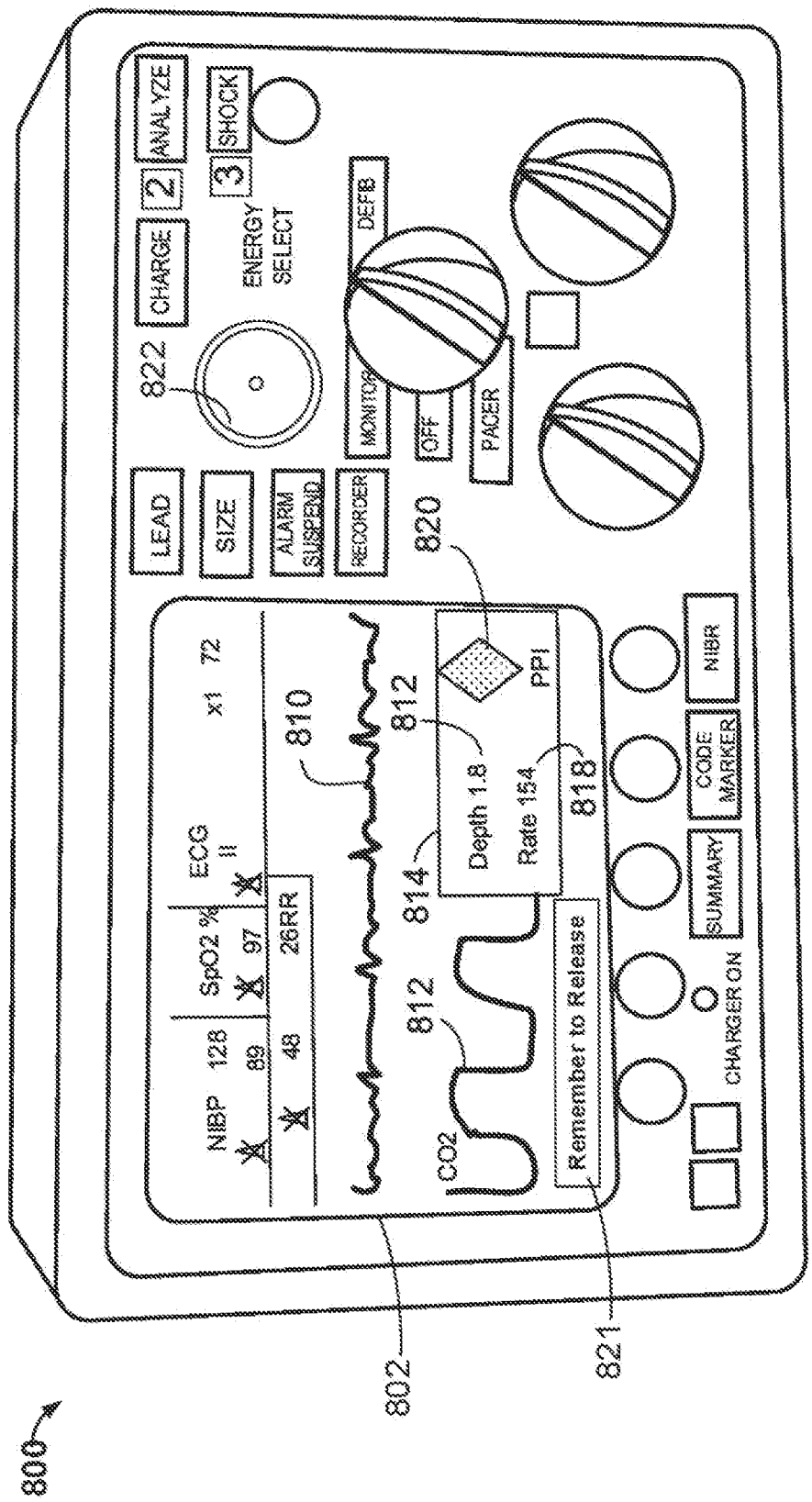
FIG. 8 illustrates a defibrillator showing some types of information that can be displayed to a rescuer.

As illustrated in FIG. 8 a defibrillator or a computing device including a display can provide real-time feedback to the rescuers. In general, the real-time feedback varies depending on an identified phase of the phases of ACD CPR chest compression treatment, e.g., one of the phases described above with respect to FIG. 1 and FIG. 2. That is, the feedback provided to the user or other device may be phase-specific, where the particular type of feedback is relevant for the specific phase of ACD therapy, according to a predetermined treatment protocol. For example, one type of feedback may be displayed if one phase has been detected, and another type of feedback may be displayed if a different phase has been detected (e.g., a transition point is detected). Feedback associated with a particular phase (e.g., data representing a template for a type of feedback to be displayed on a user interface) can be stored in data storage or associated memory and retrieved when the next phase is detected. For example, the data representing the feedback can be stored in the storage device 1330 described below with respect to FIG. 13. Hence, according to a suitable treatment protocol, when the system detects ACD therapy to be in a first phase, the system may retrieve from memory the feedback specific to the first phase and process data from the sensor(s) according to the phase-specific feedback. Similarly, when the system detects ACD therapy to be in a second phase, following the first phase, the system may retrieve from memory the feedback specific to the second phase and process data from the sensor(s) according to the phase-specific feedback.

For illustrative purposes, two particular examples of feedback are shown on a display 802 of the defibrillator 112. FIG. 8 shows a defibrillator showing some types of information that can be displayed to a rescuer. In the figure, a defibrillation device 800 with a display portion 802 provides information about patient status and CPR chest compression administration quality during the use of the defibrillator device. As shown on display 802, during the administration of chest compressions and decompressions, the device 800 displays information about the chest compressions and decompressions in box 814 on the same display as is displayed a filtered ECG waveform 810 and a CO2 waveform 812 (alternatively, an SpO2 waveform can be displayed).

During chest compressions and decompressions, the ECG waveform is generated by gathering ECG data points and accelerometer readings, and filtering the motion-induced (e.g., CPR chest compression-induced) noise out of the ECG waveform. Measurement of velocity or acceleration of chest compression during chest compressions can be performed according to the techniques taught by U.S. Pat. No. 7,220, 335, entitled "Method and Apparatus for Enhancement of Chest Compressions during Chest Compressions," the contents of which are hereby incorporated by reference in their entirety. Displaying the filtered ECG waveform helps a rescuer reduce interruptions in CPR chest compression because the displayed waveform is easier for the rescuer to decipher. If the ECG waveform is not filtered, artifacts from manual chest compressions and decompressions can make it difficult to discern the presence of an organized heart rhythm unless compressions and decompressions are halted. Filtering out these artifacts can allow rescuers to view the underlying rhythm without stopping chest compressions and decompressions.

The CPR chest compression information in box 814 is automatically displayed when compressions and decompressions are detected by a defibrillator. The information about the chest compressions and decompressions that is displayed in box 814 includes rate 818 (e.g., number of compressions and decompressions per minute) and depth 816 (e.g., depth of compressions and decompressions in inches or millimeters). The rate and depth of compressions and decompressions can be determined by analyzing accelerometer readings, or measurements from other sensor sources. Displaying the actual rate and depth data (in addition to, or instead of, an indication of whether the values are within or outside of an acceptable range) can also provide useful feedback to the rescuer. For example, if an acceptable range for chest compression depth is 2.0 to 2.4 inches, providing the rescuer with an indication that his/her compressions and decompressions are only 1.0 inch can allow the rescuer to determine how to correctly modify his/her administration of the chest compressions and decompressions (e.g., he or she can know how much to increase effort, and not merely that effort can be increased some unknown amount).

The information about the chest compressions and decompressions that is displayed in box 814 also includes a perfusion performance indicator (PPI) 820. The PPI 820 is a shape (e.g., a diamond) with the amount of fill that is in the shape differing over time to provide feedback about both the rate and depth of the compressions and decompressions. When CPR chest compression is being performed adequately, for example, at a rate of about 100 compressions and decompressions per minute (CPM) with the depth of each compression greater than 40 mm, the entire indicator will be filled. As the rate and/or depth decreases below acceptable limits, the amount of fill lessens. The PPI 820 provides a visual indication of the quality of the CPR chest compression such that the rescuer can aim to keep the PPI 820 completely filled.

As shown in display 802, the filtered ECG waveform 810 is a full-length waveform that fills the entire span of the display device, while the second waveform (e.g., the CO2 waveform 812) is a partial-length waveform and fills only a portion of the display. A portion of the display beside the second waveform provides the CPR chest compression information in box 814. For example, the display splits the horizontal area for the second waveform in half, displaying waveform 812 on left, and CPR chest compression information on the right in box 814.

The data displayed to the rescuer can change based on the actions of the rescuer. For example, the data displayed can change based on whether the rescuer is currently administering CPR chest compressions and decompressions to the patient. Additionally, the ECG data displayed to the user can change based on the detection of CPR chest compressions and decompressions. For example, an adaptive filter can automatically turn ON or OFF based on detection of whether CPR chest compression is currently being performed. When the filter is on (during chest compressions and decompressions), the filtered ECG data is displayed and when the filter is off (during periods when chest compressions and decompressions are not being administered), unfiltered ECG data is displayed. An indication of whether the filtered or unfiltered ECG data is displayed can be included with the waveform.

Also shown on the display is a reminder 821 regarding "release" in performing chest compression. Specifically, a fatigued rescuer can begin leaning forward on the chest of a patient and not release pressure on the sternum of the patient at the top of each compression. This can reduce the perfusion and circulation accomplished by the chest compressions and decompressions. The reminder 821 can be displayed when the system recognizes that release is not being achieved (e.g., signals from an accelerometer show an "end" to the compression cycle that is flat and thus indicates that the rescuer is staying on the sternum to an unnecessary degree). Such a reminder can be coordinated with other feedback as well, and can be presented in an appropriate manner to get the rescuer's attention. The visual indication can be accompanied by additional visual feedback near the rescuer's hands, and by a spoken or tonal audible feedback, including a sound that differs sufficiently from other audible feedback so that the rescuer will understand that release (or more specifically, lack of release) is the target of the feedback. For example, the defibrillator 112 can emit a sound through speaker 822 in the form of a metronome to guide the rescuer 106a in the proper rate of applying CPR chest compression.

With feedback provided at the rescuer's hands, and because the rescuer 106a is providing the chest compressions and decompressions directly with the hands, input by the system into the hands can be more directly applied with respect to the rescuer 106a keeping an appropriate pace. Such haptic feedback can also relieve the rescuer 106a of having to turn the head to view the display on defibrillator 112. Thus, a first type of feedback, such as pulsed visual, audible, or tactile feedback can be provided to guide a user in performing CPR chest compression, and that type of feedback can be interrupted and replaced with a different type of feedback such as constant sound or vibration to indicate that a rescuer is to correct a particular component of CPR chest compression (e.g., body position).

Figure 9A:
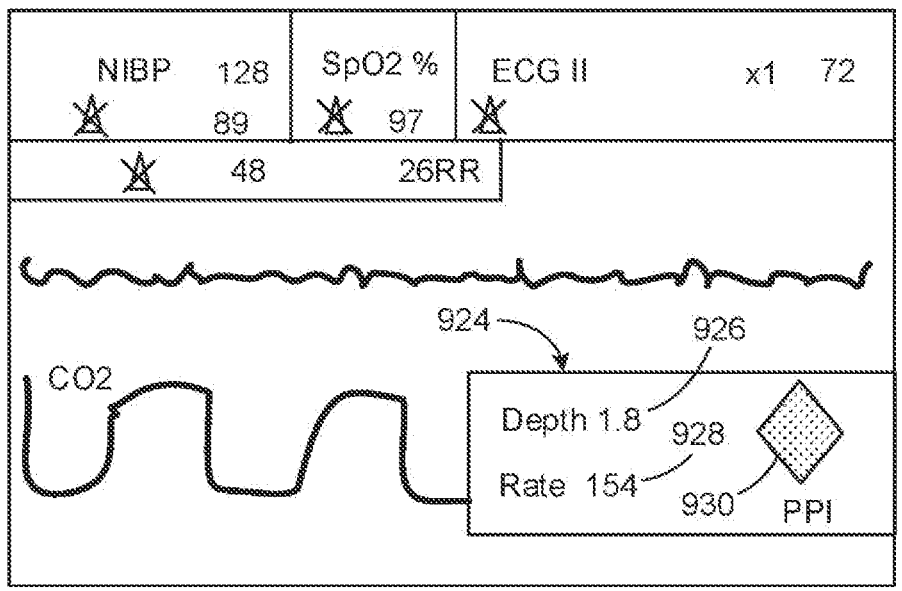
FIGS. 9A-9C show screenshots of a defibrillator display that provides feedback concerning chest compressions performed on a patient.
Figure 9B:
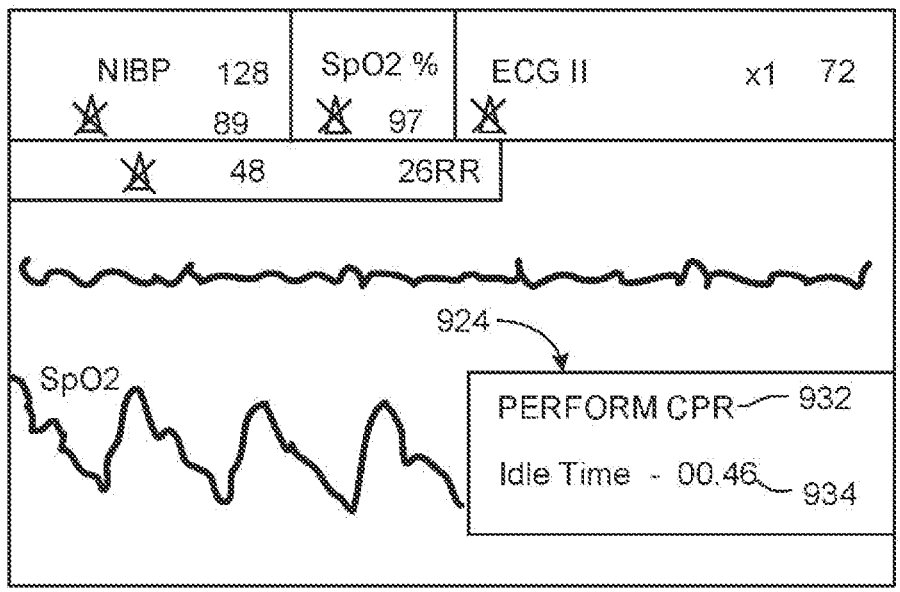
Figure 9C:
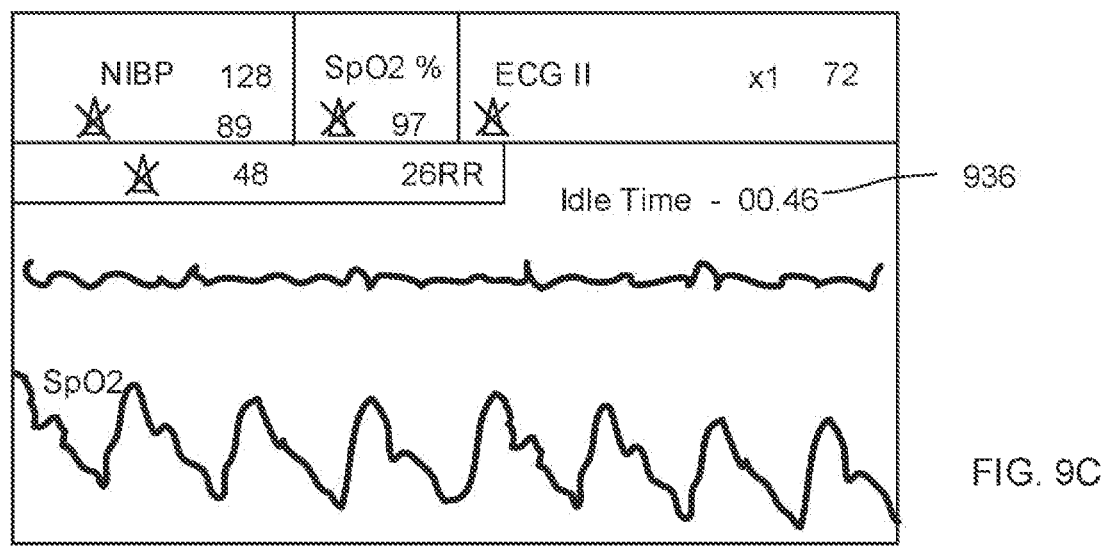

FIGS. 9A-9C show example screens that can be displayed to a rescuer on a defibrillator. Each of the displays can be supplemented with a display like box 602 in FIG. 6 when the defibrillator determines that rescuers providing some component of care (e.g., chest compressions and decompressions) can be changed.

FIG. 9A shows exemplary information displayed during the administration of CPR chest compressions and decompressions, while FIGS. 9B and 9C show exemplary information displayed when CPR chest compressions and decompressions are not being sensed by the defibrillator. The defibrillator automatically switches the information presented based on whether chest compressions and decompressions are detected. An exemplary modification of the information presented on the display can include automatically switching one or more waveforms that the defibrillator displays. In one example, the type of measurement displayed can be modified based on the presence or absence of chest compressions and decompressions. For example, CO2 or depth of chest compressions and decompressions can be displayed (e.g., a CO2 waveform 920 is displayed in FIG. 9A) during CPR chest compression administration, and upon detection of the cessation of chest compressions and decompressions, the waveform can be switched to display a SpO2 or pulse waveform (e.g., a SpO2 waveform 922 is displayed in FIG. 9B).

Another exemplary modification of the information presented on the display can include automatically adding/removing the CPR chest compression information from the display upon detection of the presence or absence of chest compressions and decompressions. As shown in FIG. 9A, when chest compressions and decompressions are detected, a portion 924 of the display includes information about the CPR chest compression such as depth 926, rate 928, and PPI 930. As shown in FIG. 9B, when CPR chest compression is halted and the system detects the absence of CPR chest compressions and decompressions, the defibrillator changes the CPR chest compression information in the portion 924 of the display, to include an indication 932 that the rescuer can resume CPR chest compression, and an indication 934 of the idle time since chest compressions and decompressions were last detected. In a similar manner, when the defibrillator determines that rescuers can change, the label 932 can change to a message such as "Change Who is Administering Compressions." In some implementations, as shown in FIG. 9C, when CPR chest compression is halted, the defibrillation device can remove the portion of the display 924 previously showing CPR chest compression data and can display a full view of the second waveform. Additionally, information about the idle time 936 can be presented on another portion of the display.

Figure 10A:
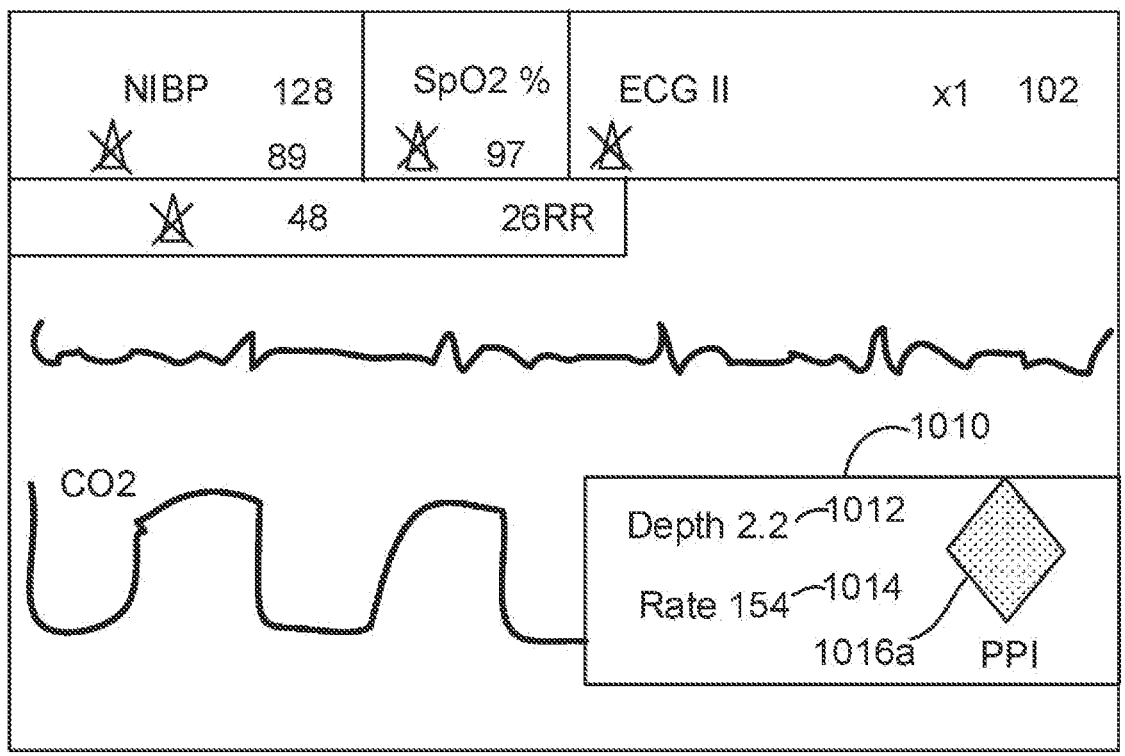
FIGS. 10A and 10B show screenshots providing feedback for CPR.
Figure 10B:
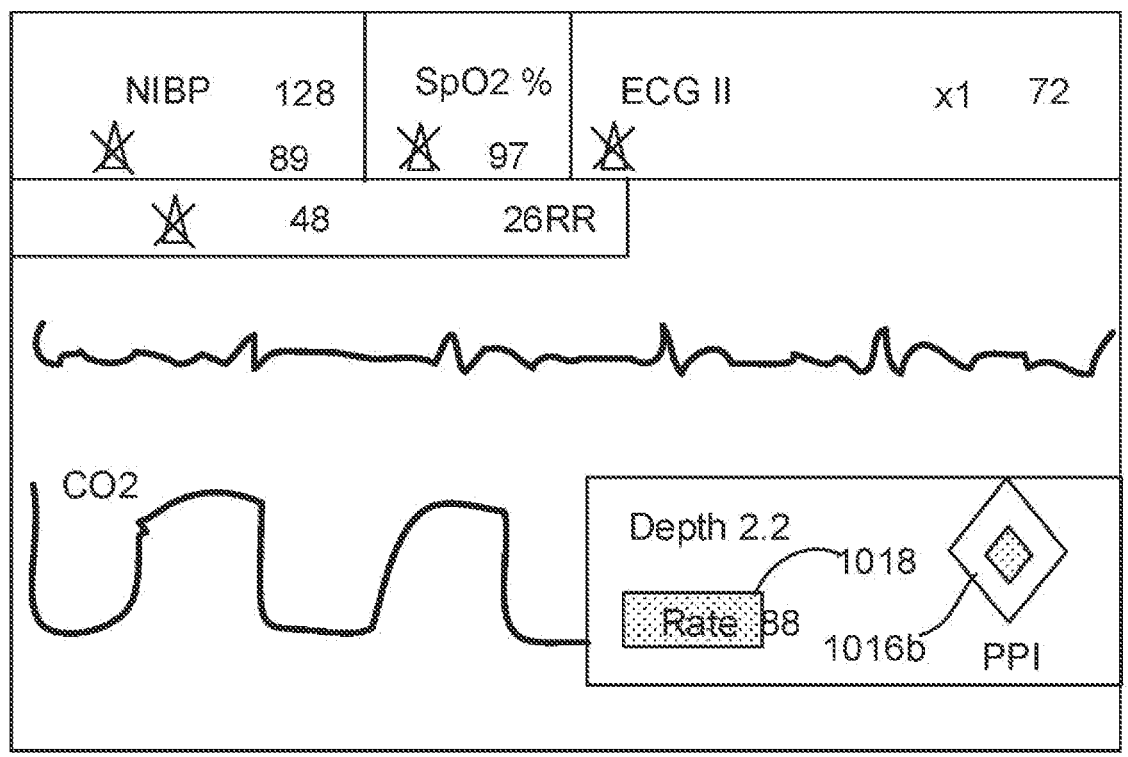

FIGS. 10A and 10B show defibrillator displays that indicate to a rescuer levels of perfusion being obtained by chest compressions and decompressions that the rescuer is performing. FIG. 10A shows exemplary data displayed during the administration of CPR chest compressions and decompressions when the CPR chest compression quality is within acceptable ranges, while FIG. 10B shows modifications to the display when the CPR chest compression quality is outside of the acceptable range.

In the example shown in FIG. 10B, the rate of chest compressions and decompressions has dropped from 80 compressions and decompressions per minute (FIG. 10A) to 60 compressions and decompressions per minute. The defibrillator device determines that the compression rate of 108 compressions and decompressions per minute is below the acceptable range of greater than 100 compressions and decompressions per minute. In order to alert the user that the compression rate has fallen below the acceptable range, the defibrillator device provides a visual indication 1018 to emphasize the rate information. In this example, the visual indication 1018 is a highlighting of the rate information. Similar visual indications can be provided based on depth measurements when the depth of the compressions and decompressions is shallower or deeper than an acceptable range of depths. Also, when the change in rate or depth indicates that a rescuer is becoming fatigued, the system can display a message to switch who is performing the chest compressions and decompressions, and can also emit aural or haptic feedback to the same effect.

In the examples shown in FIGS. 10A and 10B, a perfusion performance indicator (PPI) 1016 provides additional information about the quality of chest compressions and decompressions during CPR chest compression. The PPI 1016 includes a shape (e.g., a diamond) with the amount of fill in the shape differing based on the measured rate and depth of the compressions and decompressions. In FIG. 10A, the depth and rate fall within the acceptable ranges (e.g., at least 100 compressions and decompressions/minute (CPM) and the depth of each compression is greater than 40 mm) so the PPI indicator 1016a shows a fully filled shape. In another example, in FIG. 10B, when the rate has fallen below the acceptable range, the amount of fill in the indicator 1016b is lessened such that only a portion of the indicator is filled. The partially filled PPI 1016b provides a visual indication of the quality of the CPR chest compression is below an acceptable range.

As noted above with respect to FIG. 6A, in addition to measuring information about the rate and depth of CPR chest compressions and decompressions, in some implementations the defibrillator provides information about the active decompression. For example, as a rescuer tires, the rescuer can begin leaning on the patient between chest compressions and decompressions such that the chest cavity is not able to fully expand at the end of a compression. If the rescuer does not properly perform (portions of) chest compressions and/or decompressions the quality of the CPR chest compression can diminish. As such, providing a visual or audio indication to the user when the user does not fully release can be beneficial. In addition, such factors can be included in a determination of whether the rescuer's performance has deteriorated to a level that the rescuer can be instructed to permit someone else perform the chest compressions and decompressions, and such information can be conveyed in the various manners discussed above.

As shown in FIG. 11A, a visual representation of CPR chest compression quality can include an indicator of CPR compression-decompression parameters, such as a CPR chest compression depth/height meter 1120 and a CPR chest compression information box 1124. The CPR chest compression depth/height meter 1120 can be automatically displayed upon detection of CPR chest compressions and decompressions.

On the CPR chest compression depth/height meter 1120, a general instruction 1137 can be displayed to visually indicate an instantaneous action to be administered through the ACD CPR chest compression treatment at a particular time. That is, based on the sensed information from the ACD device, the system may provide feedback to the rescuer and/or other device for administering ACD therapy in a desirable manner, to provide as favorable patient outcomes as possible. As shown, the CPR chest compression depth/height meter 1120 may include a display that is partitioned into sections for certain phases of the ACD CPR chest compression treatment, to assist a rescuer in providing optimal therapy. For example, the system may assist the user in reaching a target release 1136 or a target depth 1140, by highlighting specific instructions for each phase. For example, the display may highlight prompts such as lift more 1135 or too shallow 1133 corresponding to the target release 1136. Or, the display may provide prompts including qualitative ACD CPR feedback, such as "good" 1131 or "too deep" 1132 when guiding the rescuer in reaching the target depth 1140. The CPR chest compression depth/height meter 1120 can be configured to display identification of a transition point 1134, to indicate the transition between different phases of the ACD CPR chest compression treatment.

Figure 11B:
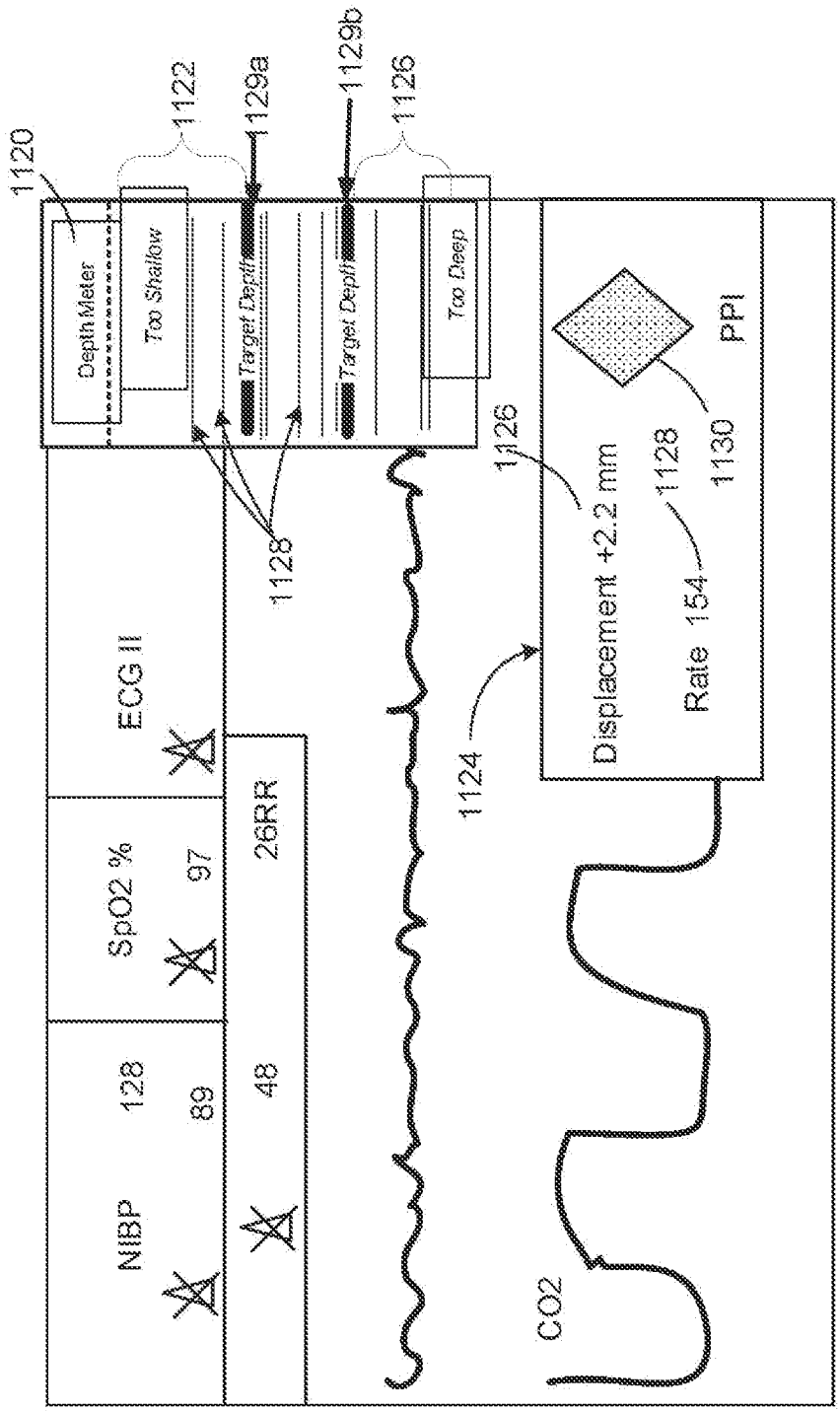

While the example shown in FIG. 11A displayed the target release 1136 and target depth 1140 as written instructions, in some additional examples, the target values can be displayed as a color or bar code corresponding to the range of preferred depths and heights. For example, multiple bars can be included on the depth meter 1120 providing an acceptable range of compression depths (e.g., as shown in FIG. 11B) and an acceptable amplitude of decompression heights. Additionally, in some implementations, compressions and decompressions that have amplitudes outside of an acceptable range can be highlighted in a different color than compressions and decompressions that have depths within the acceptable range of compression depths.

The CPR chest compression information box 1124 is automatically displayed when compressions and decompressions are detected by a defibrillator. The information about the chest compressions and decompressions that is displayed in box 1124 includes rate 1128 (e.g., number of compressions and decompressions per minute) and displacement 1126 (e.g., depth of compressions expressed as negative values and amplitude of decompressions expressed as positive values in inches or millimeters). The rate and depth of compressions and decompressions can be determined by analyzing accelerometer readings. Displaying the actual rate and displacement data (in addition to, or instead of, an indication of whether the values are within or outside of an acceptable range) can also provide useful feedback to the rescuer. For example, if an acceptable range for chest compression depth is 25 to 60 mm, providing the rescuer with an indication that his/her compressions and decompressions are only 15 mm can allow the rescuer to determine how to correctly modify his/her administration of the chest compressions and decompressions (e.g., he or she can know how much to increase effort in reaching optimal compression and decompression thresholds).

The information about the chest compressions and decompressions that is displayed box 1124 also includes a perfusion performance indicator (PPI) 1130. The PPI 1130 is a shape (e.g., a diamond) with the amount of fill that is in the shape differing over time to provide feedback about both the rate and depth of the compressions and decompressions. When CPR chest compression is being performed adequately within a range of desired parameters, for example, at a rate suitable for active compression decompression such as of about 80 compressions and decompressions per minute (CPM) with the depth of each compression falling within a desirable range for active compression decompression, the entire indicator will be filled. As the rate and/or depth falls below or exceeds above acceptable limits, the amount of fill lessens. The PPI 1130 provides a visual indication of the quality of the CPR chest compression such that the rescuer can aim to keep the PPI 1130 completely filled.

In some additional embodiments, physiological information (e.g., physiological information such as end-tidal CO2 information, arterial pressure information, volumetric CO2, pulse oximetry (presence of amplitude of waveform possibly), and carotid blood flow (measured by Doppler) of the patient (and in some cases, the rescuer) can be used to provide feedback on the effectiveness of the CPR chest compression delivered at a particular target depth. Based on the physiological information, the system can automatically determine a target CPR compression depth (e.g., calculate or look-up a new CPR compression target depth) and, for example, provide feedback to a rescuer to increase or decrease the depth/rate of the CPR compressions and decompressions. Such feedback can include a sequence of desirable positions to guide the rescuer to adjust his/her body position and/or body motion to achieve a desirable combination of CPR compressions and decompressions (e.g., depth, rate), rescuer fatigue, and/or physiological outcome. Thus, the system can provide both feedback related to how consistently a rescuer is administering CPR compressions and decompressions at a target depth/rate, and feedback related to whether the target depth/rate can be adjusted based on measured physiological parameters, along with how the rescuer may enhance his/her body positioning in administering CPR chest compression. If the rescuers do not respond to such feedback and continues performed sub-optimal CPR chest compression, the system can then display an additional message to switch out the person performing CPR chest compressions and decompressions.

In some implementations, the system regularly monitors and adjusts the target CPR compression depth. In order to determine a desirable target depth, the system makes minor adjustments to the target CPR compression depth and observes how the change in compression depth affects the observed physiological parameters before determining whether to make further adjustments to the target compression depth. More particularly, the system can determine an adjustment in the target compression depth that is a fraction of an inch or a centimeter and prompt the rescuer to increase or decrease the compression depth by the determined amount. For example, the system can adjust the target compression depth by 2.5-10 mm (e.g., 2.5 mm to 5 mm or about 5 mm) and provide feedback to the rescuer about the observed compression depth based on the adjusted target compression depth. Then, over a set period of time, the system can observe the physiological parameters and, based on trends in the physiological parameters without making further adjustments to the target compression depth and at the end of the set time period, can determine whether to make further adjustments to the target compression depth.

And again, the actual performance of the rescuer against the revised target can be continually monitored to determine when the rescuer's performance has fallen below an acceptable level, so that the rescuer and perhaps others can be notified to change who is performing the chest compressions and decompressions. Also, each of the relevant parameters of patient condition discussed above with respect to the various screenshots can be made one of multiple inputs to a process for determining when rescuers who are performing one component of a rescue technique can be switched out with another rescuer, such as for reasons of apparent fatigue on the part of the first rescuer.

While at least some of the embodiments described above describe techniques and displays used during manual human-delivered chest compressions and decompressions, similar techniques and displays can be used with automated chest compression devices such as the AUTOPULSE device manufactured by ZOLL Medical, MA.

Figure 12:
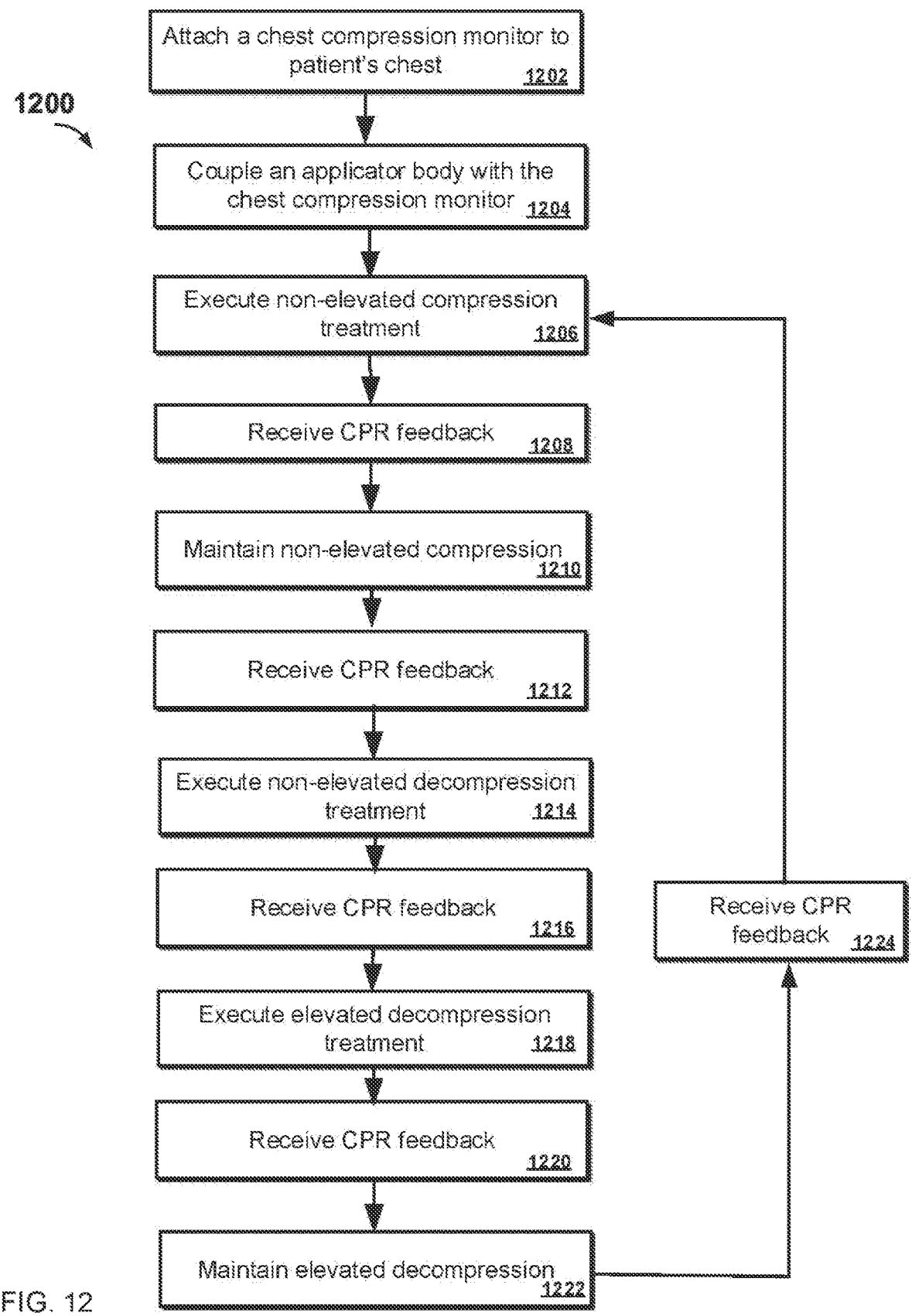
FIG. 12 shows an example of a flowchart of a process for providing feedback to a user during the performance of ACD CPR chest compression treatment.

FIG. 12 shows an example flowchart 1200. At step 1202, a chest compression monitor is attached to a patient's chest. The chest compression monitor can be configured to display information that can assist with an ACD CPR treatment to be performed, as described with reference to FIGS. 3, 5, and 11. At step 1204, an applicator body is coupled with the chest compression monitor and at least one sensor is attached to the patient's chest. The sensor includes at least one of a motion sensor and a force sensor. The motion sensor can measure the at least one parameter related to the ACD CPR treatment. The force sensor can measure the at least one parameter related to the ACD CPR treatment. The motion sensor can measure the information for determining whether at least one transition point of the ACD CPR treatment has been reached. The motion sensor can include one or more accelerometers configured to detect an acceleration signal associated with the displacement of the at least the portion of the patient's chest. A first accelerometer can be configured to detect an acceleration signal associated with displacement of a first portion of the patient's chest and a second accelerometer can be configured to detect an acceleration signal associated with displacement of a second portion of the patient's chest.

At step 1206, the ACD CPR treatment is initiated by executing a non-elevated compression treatment that starts from a neutral point of the patient's chest and continues until a transition point is identified. The information for determining whether the at least one transition point has been reached can include at least one of displacement information and force information. At step 1208, feedback is received real-time, such as from a storage device based on the detected phase (e.g., non-elevated compression phase), as described with reference to FIG. 13. The feedback can be phase specific. The feedback can assist with the phase specific (e.g., non-elevated compression) treatment, as described with reference to FIGS. 3, 5, and 11. For example, the feedback signal can include providing a prompt to maintain at least one of a compression force, increase in compression depth and a compression rate according to the desired treatment protocol. The prompt to maintain at least one of a compression force and a compression rate can include at least one of an audio prompt, a verbal prompt, a non-verbal prompt, a visual prompt, a graphical prompt and a haptic prompt. The prompt to maintain at least one of a compression force and a compression rate can include a signal for operating an automated compressor. The feedback signal can include information regarding patient's chest displacement below the neutral point (e.g., rib displacement below a breakage point) and a warning for the rescuer to limit the compression force applied, so that excess force is not applied to the ribs to prevent breakage of the patient's ribs. In some implementations, the feedback associated with non-elevated compression is stored to be accessible at a later time.

At 1210, a non-elevated compression is maintained. The hold time of the maintained non-elevated compression can be between about 20-100 milliseconds, about 50-200 milliseconds, or about 10-1000 milliseconds. The hold time can be sufficient to promote net blood flow to the head of the patient. At step 1212, CPR feedback is received. The feedback signal can include at least one of an audio prompt, a verbal prompt, a non-verbal prompt, a visual prompt, a graphical prompt and a haptic prompt indicating the timing, during which non-elevated compression is maintained. In some implementations, the feedback associated with maintained non-elevated compression is stored to be accessible at a later time.

At step 1214, a non-elevated decompression treatment is executed. At step 1216, CPR feedback is received. The feedback signal can include providing a prompt to apply a desired release velocity during decompression upstroke for providing a negative intrathoracic pressure according to the desired treatment protocol. The prompt to maintain the desired release velocity can include at least one of an audio prompt, a verbal prompt, a non-verbal prompt, a visual prompt, a graphical prompt and a haptic prompt. The prompt to maintain the desired release velocity can include a signal for operating an automated compressor. In some implementations, the feedback associated with non-elevated decompression is stored to be accessible at a later time.

At step 1218, an elevated decompression treatment is executed. At step 1220, CPR feedback is received. The feedback signal can include providing a prompt to apply a sufficient release velocity during decompression upstroke for providing a negative intrathoracic pressure according to the desired treatment protocol. The at least one parameter related to the ACD CPR treatment can include at least one of displacement, velocity, acceleration, time, work, power, pressure, direction and orientation. The parameter provided by the feedback signal can be selected based on a comparison of one or more parameters with particular ranges and thresholds. For example, each of the measured parameters (displacement, velocity, acceleration, time, work, power, pressure, direction and orientation) can be compared to a corresponding preset range or threshold and upon detection that a parameter is out of range a feedback signal is generated to provide an alert and guidance for a corrective action (e.g., increase or decrease of a particular parameter). The feedback signal can include providing a prompt to maintain the applicator device according to a desired orientation and direction during application of the ACD CPR treatment to ensure optimal application of force while reducing risk of rib and/or skin injury. The feedback signal can include a prompt to increase at least one of displacement, velocity, acceleration, power, pressure or force applied to the patient's chest during decompression upstroke to reach a target decompression level within an optimal period of time (e.g., that enables optimal vascularization and oxygenation). The feedback signal can include a prompt to limit at least one of displacement, velocity, acceleration, power, pressure or force applied to the patient's chest during decompression upstroke for reducing risk of rib and/or skin injury according to the desired treatment protocol. The prompt to limit a force applied to the patient's chest during decompression upstroke can include at least one of an audio prompt, a verbal prompt, a non-verbal prompt, a visual prompt, a graphical prompt and a haptic prompt. The prompt to limit a force applied to the patient's chest during decompression upstroke can include a signal for operating an automated compressor. The feedback signal can include providing a prompt to ventilate during decompression upstroke. The prompt to ventilate can include at least one of an audio prompt, a verbal prompt, a non-verbal prompt, a visual prompt, a graphical prompt and a haptic prompt. The prompt to ventilate can include a signal for operating an automated ventilator. In some implementations, the feedback associated with elevated decompression is stored to be accessible at a later time.

At step 1222, an elevated compression is maintained. The hold time of the maintained elevated compression can be between about 50-200 milliseconds. The hold time can be sufficient to promote net blood flow to the heart of the patient. At step 1224, feedback is received indicating continuing ACD CPR chest compression treatment (returning to step 1206) or interrupting ACD CPR chest compression treatment. In some implementations, the feedback associated with maintained elevated decompression is stored to be accessible at a later time.

Since the time intervals between the various phases e.g. 1206, 1210, 1214, 1218, 1222 of the compression cycle can be closely-spaced in time, the rescuer delivering compressions will not be able to properly receive the information and respond to the feedback and otherwise interact substantially instantaneously with the feedback, due to natural human delay. The CPR feedback may be generated and received after the completion of two or more phases 102, 104, 106, 108 of the compression cycle. The feedback may also be the aggregation, either statistically or other mathematical operation of two or more cycles of a measured parameter of a particular phase, so as to sufficiently allow the rescuer to respond to the feedback in a timely manner. For instance, the statistical operation might be mean, median, maximum, minimum, variance of the associated feedback parameters. A mathematical operation might be sum. The measured parameter might be maximum velocity, minimum velocity, maximum force, minimum force, distance, and/or other appropriate measure. The CPR feedback may be generated and received after the detected conclusion of one or more chest compression cycles.

Figure 13:
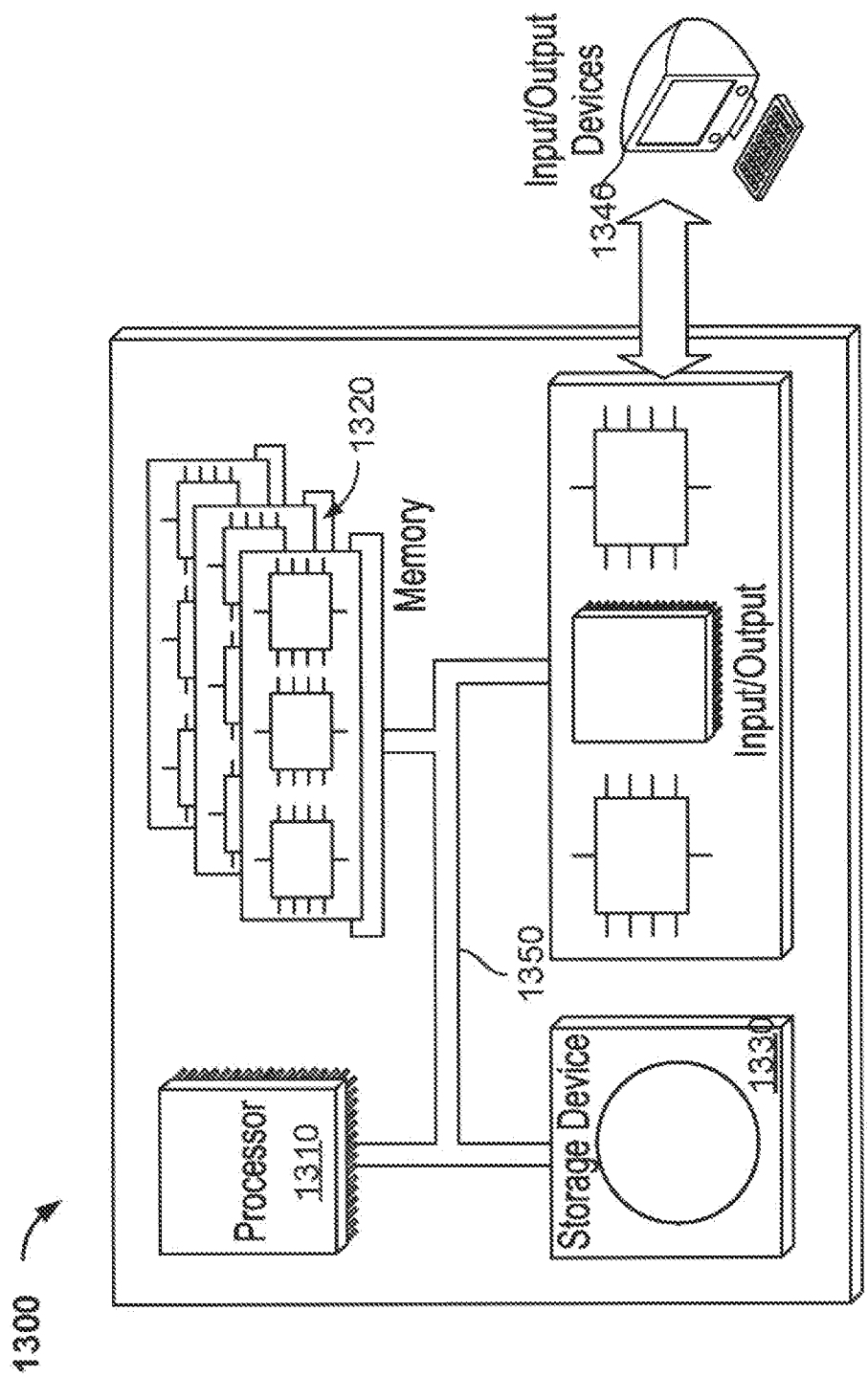
FIG. 13 shows a general computer system that can provide interactivity with a user of a medical device, such as feedback to a user in the performance of CPR chest compression treatment.

FIG. 13 shows a computer system 1300 that could be a component of, for example, a defibrillator (e.g., the defibrillator 112 shown in FIG. 3) or an ACD device (e.g., the ACD device 208 shown in FIG. 4, or processor circuit 535 in FIG. 5B) or another kind of computer system (e.g., the computer system 110 shown in FIG. 3). The computer system 1300 can be used, for example, for computing the quality of one or more components of ACD CPR chest compression provided to a patient and generating feedback to rescuers, including feedback to change rescuers who are performing some components of the CPR chest compression. The system 1300 can be implemented in various forms of digital computers, including computerized defibrillators laptops, personal digital assistants, tablets, and other appropriate computers. Additionally, the system can include portable storage media, such as, Universal Serial Bus (USB) flash drives. For example, the USB flash drives can store operating systems and other applications. The USB flash drives can include input/output components, such as a wireless transmitter or USB connector that can be inserted into a USB port of another computing device.

The system 1300 includes a processor 1310, a memory 1320, a storage device 1330, and an input/output device 1340. Each of the components 1310, 1320, 1330, and 1340 are interconnected using a system bus 1350. The processor 1310 is capable of processing instructions for execution within the system 1300. The processor can be designed using any of a number of architectures. For example, the processor 1310 can be a CISC (Complex Instruction Set Computers) processor, a RISC (Reduced Instruction Set Computer) processor, or a MISC (Minimal Instruction Set Computer) processor.

In one implementation, the processor 1310 is a single-threaded processor. In another implementation, the processor 1310 is a multi-threaded processor. The processor 1310 is capable of processing instructions stored in the memory 1320 or on the storage device 1330 to display graphical information for a user interface on the input/output device 1340.

The memory 1320 stores information within the system 1300. In one implementation, the memory 1320 is a computer-readable medium. In one implementation, the memory 1320 is a volatile memory unit. In another implementation, the memory 1320 is a non-volatile memory unit.

The storage device 1330 is capable of providing mass storage for the system 1300. In one implementation, the storage device 1330 is a computer-readable medium. In various different implementations, the storage device 1330 can be flash storage, a hard disk device, an optical disk device, or a tape device.

The input/output device 1340 provides input/output operations for the system 1300. In one implementation, the input/output device 1340 includes a keyboard and/or pointing device. In another implementation, the input/output device 1340 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described can be employed, and can be encompassed by the following claims.

What is claimed is:

1. An apparatus for automatically providing an active compression decompression (ACD) cardiopulmonary resuscitation (CPR) treatment to a patient in need of emergency assistance, the apparatus comprising:
   one or more sensors, wherein at least one sensor of the one or more sensors is configured to be coupled to the patient's chest and to measure force applied during the ACD CPR treatment to the patient's chest, wherein the ACD CPR treatment is applied in a continuous variation of phases, the phases comprising at least an elevated compression phase, a non-elevated compression phase, an elevated decompression phase, and a non-elevated decompression phase; and
   one or more processors and a non-transitory computer readable storage medium encoded with a computer program comprising instructions that, when executed, cause the one or more processors to perform operations comprising:
   processing the measured force during application of the ACD CPR treatment,
   determining, based on the processed force, a neutral point associated with a zero force being exerted on the patient's chest during the ACD CPR treatment,
   determining, based on the processed force and the determined neutral point, whether at least one transition point between a current phase and a next phase in the ACD CPR treatment has been reached, and
   in response to determining that the transition point between the current phase and the next phase in the ACD CPR treatment has been reached, adjusting one or more application parameters for the ACD CPR treatment.

2. The apparatus of claim 1, comprising a piston configured to apply the force on the at least a portion of the patient's chest according to the one or more application parameters.

3. The apparatus of claim 2, wherein the at least one sensor is included at a distal end of the piston.

4. The apparatus of claim 1, wherein the at least one sensor comprises a force sensor or a pressure sensor.

5. The apparatus of claim 1, wherein processing the force during the ACD CPR treatment comprises determining a force amplitude, an impulse, a distance, an average force, or a peak force.

6. The apparatus of claim 1, wherein processing the force during the ACD CPR treatment comprises comparing the force to a threshold.

7. The apparatus of claim 1, wherein processing the force during the ACD CPR treatment comprises determining a compliance of the patient's chest wall.

8. The apparatus of claim 1, wherein adjusting the one or more application parameters for the ACD CPR treatment to correspond to the subsequent phase of the ACD CPR treatment comprises a gradual variation of the force and a hold time with the force at a constant level.

9. The apparatus of claim 1, wherein the one or more application parameters comprise a release velocity during decompression upstroke for providing a negative intrathoracic pressure according to a treatment protocol.

10. The apparatus of claim 1, wherein the one or more application parameters comprise the force to be applied to the patient's chest during decompression upstroke according to a desired treatment protocol.

11. The apparatus of claim 1, wherein the one or more application parameters comprise at least one of displacement, velocity, acceleration, time, work, power, pressure, direction, and orientation.

12. The apparatus of claim 1, wherein the one or more application parameters comprise a distance above the neutral point and a depth of compression below the neutral point.

13. The apparatus of claim 12, wherein the at least one transition point is at least one of between an elevated compression phase and a non-elevated compression phase, between the elevated decompression phase and the elevated compression phase, between the elevated decompression phase and a hold time above the neutral point, and between a hold time above the neutral point and the elevated compression phase.

14. The apparatus of claim 13, wherein the hold time is between about 50-200 milliseconds.

15. The apparatus of claim 12, wherein the at least one transition point is at least one of between the non-elevated compression phase and the non-elevated decompression phase, between the non-elevated compression phase and a hold time below the neutral point, and between hold time below the neutral point and the non-elevated decompression phase.

16. The apparatus of claim 15, wherein the hold time is between about 50-200 milliseconds.

17. The apparatus of claim 1, wherein the at least one transition point is between the non-elevated decompression phase and the elevated decompression phase.

18. The apparatus of claim 1, wherein the at least one transition point between the current phase and the next phase in the ACD CPR treatment comprises zero static compression force and zero static decompression force being exerted on to the patient's chest during the ACD CPR treatment.

19. The apparatus of claim 1, comprising a user interface configured to display the one or more application parameters during the ACD CPR treatment.

20. The apparatus of claim 19, wherein the user interface is configured for displaying at least one of information representing effectiveness of CPR and an indication of a phase of the ACD CPR treatment.

21. The apparatus of claim 20, wherein the user interface is configured to be displayed on a device external to the apparatus comprising at least one of a smartphone, a smartwatch, a tablet device, a monitor, a diagnostic device, and a defibrillator.

22. The apparatus of claim 1, comprising an adhesive pad configured to be adhered to at least a portion of a patient's chest.

23. The apparatus of claim 22, wherein the adhesive pad comprises pressure-sensitive adhesives comprising medical bandage adhesives, or transdermal patches.

24. The apparatus of claim 22, wherein the adhesive pad is configured to transfer a decompression force between the apparatus and the patient's chest during the ACD CPR treatment without detaching.

25. The apparatus of claim 1, comprising a portable device.

26. The apparatus of claim 1, wherein determining whether the at least one transition point has been reached comprises:
   wherein the neutral point changes over a course of the ACD CPR treatment, and
   determining, based on the neutral point, whether the at least one transition point between the current phase and the next phase in the ACD CPR treatment has been reached.

27. The apparatus of claim 1, wherein the one or more application parameters for the ACD CPR treatment are adjusted to correspond to a subsequent phase of the ACD CPR treatment.

28. The apparatus of claim 1, further comprising a second sensor of the one or more sensors, wherein the second sensor is configured to be coupled to the patient's chest and to measure a displacement of the patient's chest during the ACD CPR treatment.

29. The apparatus of claim 28, wherein the second sensor comprises an accelerometer.

30. The apparatus of claim 28, wherein determining whether at least one transition point between a current phase and the next phase in the ACD CPR treatment further comprises:
   determining a displacement for the patient's chest based at least on data obtained from the one or more sensors, and
   determining the neutral point based on the determined displacement.

31. The apparatus of claim 1, wherein determining whether at least one transition point between a current phase and a next phase in the ACD CPR treatment has been reached is responsive to when the determined neutral point is different than a prior neutral point.

* * * * *